United States Patent [19]

Petrillo, Jr.

[11] 4,374,131
[45] Feb. 15, 1983

[54] AMINO AND SUBSTITUTED AMINO PHOSPHINYL-ALKANOYL COMPOUNDS

[75] Inventor: Edward W. Petrillo, Jr., Pennington, N.J.

[73] Assignee: E. R. Squibb & Sons, Inc., Princeton, N.J.

[21] Appl. No.: 258,194

[22] Filed: Apr. 27, 1981

[51] Int. Cl.³ .................. A61K 31/675; C07F 9/30; C07F 9/32
[52] U.S. Cl. .................. 424/200; 260/941; 260/942; 546/15; 546/22; 546/24; 548/112; 548/409; 548/413; 549/6; 549/218; 560/137; 560/157; 562/443; 562/553
[58] Field of Search ............ 424/200; 546/522, 24; 548/409, 413, 112

[56] References Cited

U.S. PATENT DOCUMENTS

| | | | |
|---|---|---|---|
| 4,105,776 | 8/1978 | Ondetti et al. | 424/274 |
| 4,129,566 | 12/1978 | Ondetti et al. | 546/326 |
| 4,151,172 | 4/1979 | Ondetti et al. | 260/326.2 |
| 4,154,935 | 5/1979 | Ondetti et al. | 546/189 |
| 4,168,267 | 9/1979 | Petrillo | 260/326.2 |
| 4,192,878 | 3/1980 | Ondetti | 424/270 |
| 4,217,359 | 8/1980 | Krapcho | 424/274 |
| 4,234,489 | 11/1980 | Ondetti et al. | 260/326.42 |
| 4,316,896 | 2/1982 | Thorsett et al. | 424/200 |
| 4,316,905 | 2/1982 | Krapcho | 424/274 |
| 4,329,473 | 5/1982 | Almquist et al. | 546/281 |
| 4,337,201 | 6/1982 | Petrillo | 548/413 |

FOREIGN PATENT DOCUMENTS

| | | |
|---|---|---|
| 868532 | 10/1978 | Belgium . |
| 2027025 | 2/1980 | United Kingdom . |
| 2028327 | 3/1980 | United Kingdom . |
| 2039478 | 8/1980 | United Kingdom . |

OTHER PUBLICATIONS

Mauger et al., "Analogs and Homologs of Proline and Hydroxyproline" Chem. Review, vol. 66, pp. 47–86 (1966).

*Primary Examiner*—Richard Raymond
*Attorney, Agent, or Firm*—Lawrence S. Levinson; Stephen B. Davis

[57] ABSTRACT

Compounds of the formula

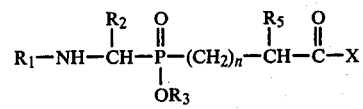

wherein X is an imino acid or ester and $R_1$ is hydrogen,

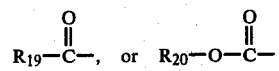

are useful hypotensive agents due to their angiotensin converting enzyme inhibition activity.

37 Claims, No Drawings

AMINO AND SUBSTITUTED AMINO PHOSPHINYL-ALKANOYL COMPOUNDS

BACKGROUND OF THE INVENTION

Petrillo in U.S. Pat. No. 4,168,267 discloses that various phosphinylalkanoyl substituted prolines are useful as hypotensive agents due to their ability to inhibit the angiotensin converting enzyme.

Ondetti et al. in U.S. Pat. No. 4,151,172 discloses that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti et al. in U.S. Pat. No. 4,105,776 disclose such compounds wherein the proline ring is unsubstituted or substituted by an alkyl or hydroxy group. Ondetti et al. in U.S. Pat. No. 4,154,935 disclose such compounds wherein the proline ring is substituted with one or more halogens. Ondetti et al. in U.K. patent application No. 2,028,327 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.K. patent application No. 2,039,478 discloses such compounds wherein the proline ring has a diether, dithioether, ketal or thioketal substituent in the 4-position. Krapcho in U.S. Ser. No. 164,985 filed July 1, 1980, now U.S. Pat. No. 4,316,905, discloses such compounds wherein the proline ring has a cycloalkyl, phenyl, or phenyl-lower alkylene substituent. Ondetti et al. in U.S. Pat. No. 4,234,489 disclose such compounds wherein the proline has a keto substituent in the 5-position. Krapcho et al. in U.S. Ser. No. 162,341 filed June 23, 1980 now U.S. Pat. No. 4,310,461 disclose such compounds wherein the proline has an imido, amido, or amino substituent in the 4-position. Iwao et al. in U.K. patent application No. 2,027,025 disclose such compounds wherein the proline has an aromatic substituent in the 5-position.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgian Pat. No. 868,532.

SUMMARY OF THE INVENTION

This invention is directed to new amino and substituted amino phosphinylalkanoyl compounds of formula I and salts thereof $$R_1-NH-CH(R_2)-P(O)(OR_3)-(CH_2)_n-CH(R_5)-C(O)-X. \quad (I)$$

X is an imino acid of the formula

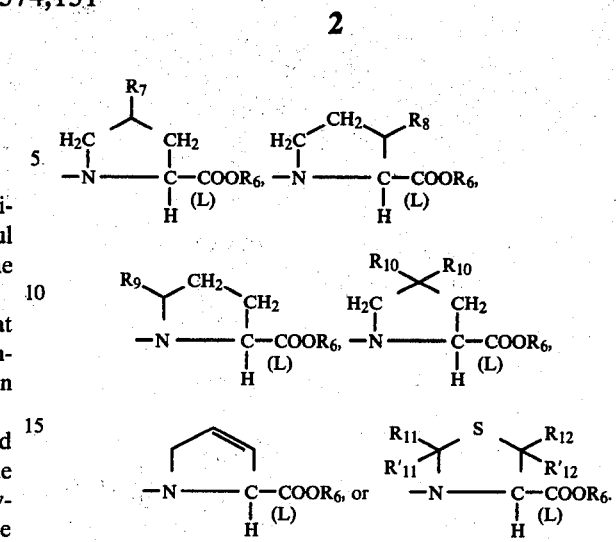

$R_7$ is hydrogen, lower alkyl, halogen, keto, hydroxy, $-NH-\overset{O}{\underset{\|}{C}}-$lower alkyl, azido,

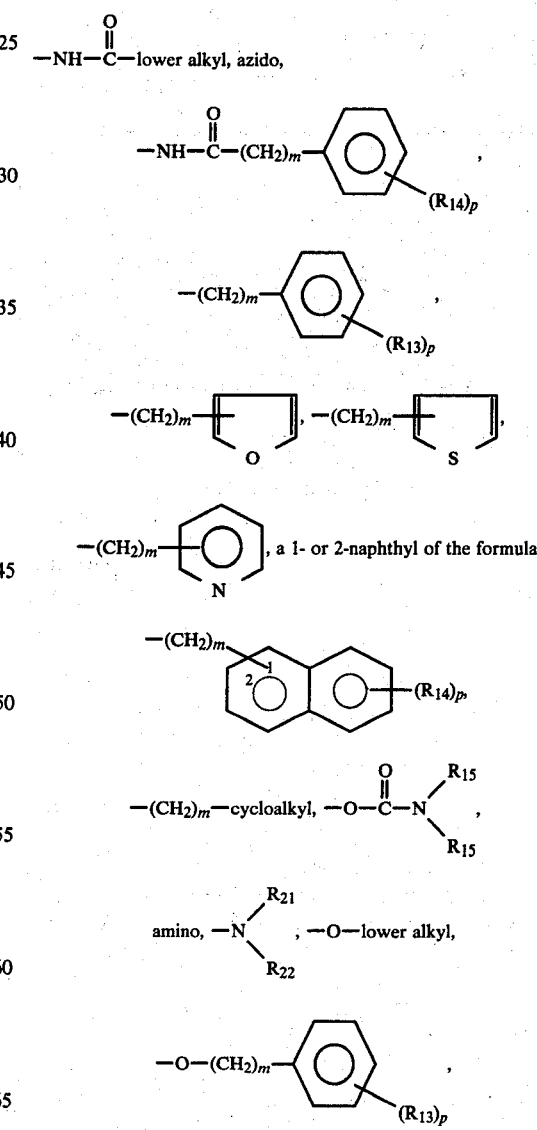

a 1- or 2-naphthyloxy of the formula

-continued

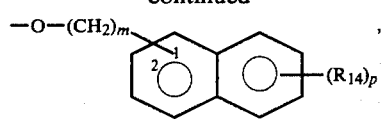

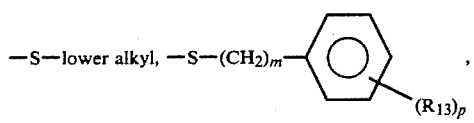

or a 1- or 2-naphthylthio of the formula

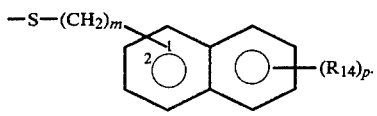

R$_8$ is keto, halogen,

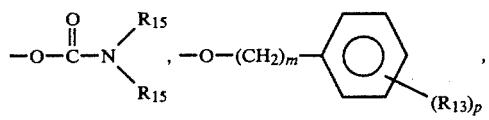

—O—lower alkyl, a 1- or 2-naphthyloxy of the formula

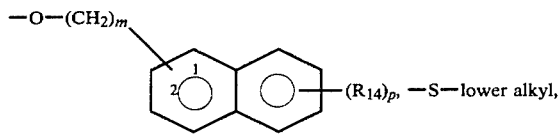

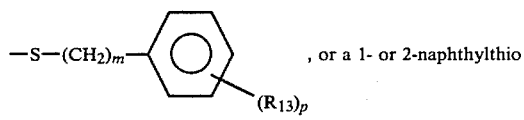, or a 1- or 2-naphthylthio of the formula 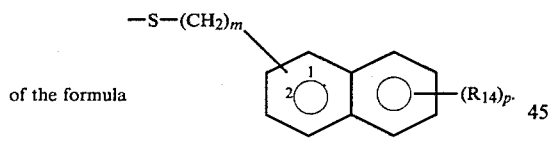

R$_9$ is keto or

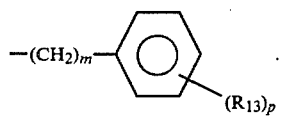

R$_{10}$ is halogen or —Y—R$_{16}$.

R$_{11}$, R$_{11}'$, R$_{12}$ and R$_{12}'$ are independently selected from hydrogen and lower alkyl or R$_{11}'$, R$_{12}$ and R$_{12}'$ are hydrogen and R$_{11}$ is

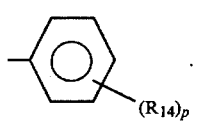

R$_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

R$_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two or three.

p is one, two or three provided that p is more than one only if R$_{13}$ or R$_{14}$ is hydrogen, methyl, methoxy, chloro, or fluoro.

R$_{15}$ is hydrogen or lower alkyl of 1 to 4 carbons.

Y is oxygen or sulfur.

R$_{16}$ is lower alkyl of 1 to 4 carbons,

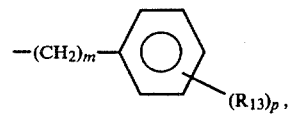

or the R$_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

n is zero or one.

R$_5$ is hydrogen, lower alkyl, halo substituted lower alkyl, benzyl or phenethyl.

R$_3$ and R$_6$ are independently selected from hydrogen, lower alkyl, benzyl, benzhydryl, or

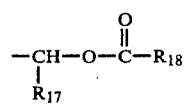

wherein R$_{17}$ is hydrogen, lower alkyl, or phenyl, and R$_{18}$ is hydrogen, lower alkyl, lower alkoxy, phenyl, or R$_{17}$ and R$_{18}$ taken together are —(CH$_2$)$_2$—, —(CH$_2$)$_3$—, —CH=CH—, or

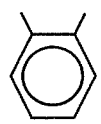

R$_1$ is hydrogen,

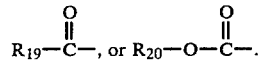

R$_{19}$ is hydrogen, lower alkyl, halo substituted lower alkyl, amino substituted lower alkyl,

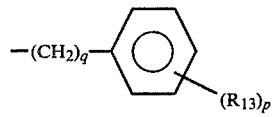

wherein R$_{13}$ and p are as defined above and q is zero or an integer from 1 to 7, cycloalkyl,

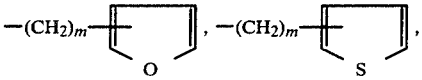

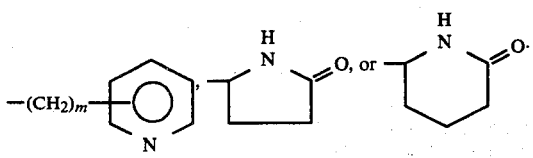

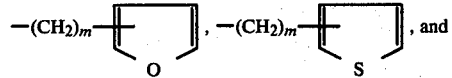

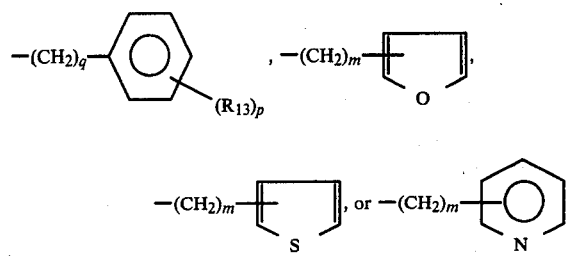

$R_{20}$ is lower alkyl, phenyl, benzyl or phenethyl.

$R_2$ is hydrogen, lower alkyl, lower alkenyl, halo substituted lower alkyl,

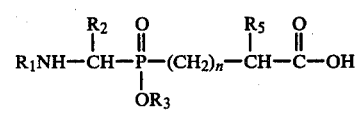

wherein q, $R_{13}$, p and m are as defined above.

$R_{21}$ is lower alkyl, benzyl, or phenethyl.

$R_{22}$ is hydrogen, lower alkyl, benzyl or phenethyl.

DETAILED DESCRIPTION OF THE INVENTION

This invention in its broadest aspects relates to the amino and substituted amino phosphinylalkanoyl compounds of formula I above, to compositions containing such compounds and to the method of using such compounds as anti-hypertensive agents, and to intermediates useful in preparing such compounds.

The term lower alkyl used in defining various symbols refers to straight or branched chain hydrocarbon radicals having up to ten carbons, for example, methyl, ethyl, propyl, isopropyl, butyl, isobutyl, t-butyl, pentyl, isopentyl, etc. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term lower alkenyl refers to straight or branched chain hydrocarbon radicals of 2 to 7 carbons, preferably 2 to 5 carbons, having at least one double bond, for example ethenyl, propenyl, 2-butenyl, etc.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term amino substituted lower alkyl refers to such lower alkyl groups described above in which one or more hydrogens have been replaced by an amino group such as aminomethyl, 1-aminoethyl, 2-aminoethyl, etc.

The symbols represent that the alkylene bridge is attached to an available carbon atom.

The compounds of formula I are prepared according to the following procedures. An acid or its activated form of formula II wherein $R_1$ is other than hydrogen and $R_3$ is hydrogen, lower alkyl, benzyl, or benzhydryl $$R_1NH-\overset{R_2}{\underset{}{CH}}-\overset{O}{\underset{OR_3}{P}}-(CH_2)_n-\overset{R_5}{\underset{}{CH}}-\overset{O}{\underset{}{C}}-OH \quad \text{(II)}$$

is coupled with an imino acid or ester of the formula $$HX \quad \text{(III)}$$

The term activated form refers to the conversion of the acid to a mixed anhydride, symmetrical anhydride, acid chloride, or activated ester, see Methoden der Organischen Chemie (houben-Weyl), Vol. XV, part II, page 1 et seq. (1974) for a review of the methods of acylation. Preferably, the reaction is performed in the presence of a coupling agent such as 1,1-carbonyldiimidazole, or dicyclohexylcarbodiimide.

The compounds of formula I wherein $R_1$ is hydrogen are prepared by coupling an acid of formula II wherein $R_1$ is

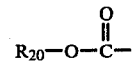

with the appropriate imino acid ester of formula III. Deprotection of the resulting product, for example, by treating with hydrogen gas in the presence of a palladium on carbon catalyst when $R_{20}$ is benzyl yields the product wherein $R_1$ is hydrogen.

Similarly, the products of formula I wherein either or both of $R_3$ and $R_6$ are lower alkyl, benzyl, or benzhydryl can be hydrogenated as described above or chemically treated such as with trifluoroacetic acid and anisole to yield the products of formula I wherein $R_3$ and $R_6$ are hydrogen.

The ester products of formula I wherein $R_6$ is

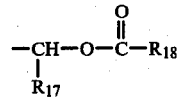

may be obtained by employing the imino acid of formula III in the coupling reaction with the ester group already in place. Such ester starting materials can be prepared by treating the imino acid with an acid chloride such as

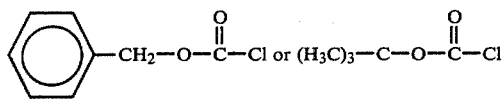

so as to protect the N-atom. The protected imino acid is then reacted in the presence of base with a compound of the formula

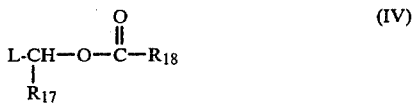  (IV)

wherein L is a leaving group such as chlorine, bromine, tolylsulfonyl, etc., followed by removal of the N-protecting group such as by treatment with acid or hydrogenation.

The ester products of formula I wherein $R_6$ is

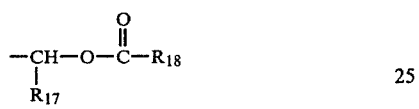

can also be obtained by treating the product of formula I wherein $R_6$ is hydrogen with a molar equivalent of the compound of formula IV. The diester products wherein $R_3$ and $R_6$ are the same and are

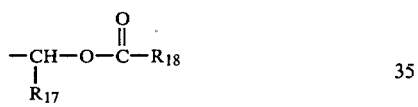

can be obtained by treating the product of formula I wherein $R_3$ and $R_6$ are both hydrogen with two or more equivalents of the compound of formula IV.

The ester products of formula I wherein $R_3$ is

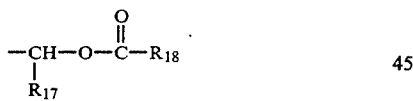

can be obtained by treating the product of formula I wherein $R_3$ is hydrogen and $R_6$ is t-butyl, benzyl or benzhydryl with the compound of formula IV in the presence of base. Removal of the $R_6$ ester group such as by hydrogenation yields the products of formula I wherein $R_3$ is

and $R_6$ is hydrogen.

The products of formula I wherein $R_1$ is hydrogen can be employed as intermediates to yield the products of formula I wherein $R_1$ is

In this procedure the compound of formula I is coupled with an acid or its activated form of the formula

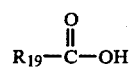

preferably in the presence of a coupling agent.

The products of formula I wherein $R_7$ is amino may be obtained by reducing the corresponding products of formula I wherein $R_7$ is azido.

The products of formula I wherein $R_7$ is the substituted amino group,

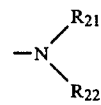

may be obtained by treating the corresponding 4-keto product of formula I with the amine,

in the presence of hydrogen and catalyst or in the presence of sodium cyanotrihydridoborate. Also, the substituted amino products of formula I wherein $R_{22}$ is other than hydrogen may be obtained by treating the corresponding 4-amino product of formula I with the ketone,

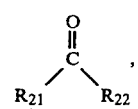

in the presence of hydrogen and catalyst or in the presence of sodium cyanotrihydridoborate.

The carboxylic acids of formula II wherein $R_1$ is other than hydrogen can be prepared by various procedures. For example, the substituted amine of the formula $R_1NH_2$  (VI)

can be treated with the aldehyde of the formula $R_2$—CHO  (VII)

and the dichlorophosphine

  (VIII)

to yield the intermediate

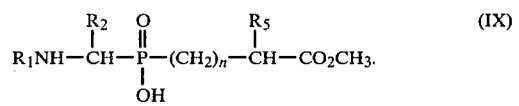  (IX)

The intermediate of formula IX can be saponified such as by treatment with sodium hydroxide to yield the desired acid of formula II wherein $R_3$ is hydrogen or esterified such as by treatment with PCl$_5$ or an alkyl chloroformate followed by the appropriate alcohol, treatment with a reagent such as diazomethane, 1-benzyl-3-p-tolyltriazine, etc., followed by saponification to yield the acid of formula II wherein R$_3$ is lower alkyl, benzyl, or benzhydryl.

The carboxylic acids of formula II wherein n is zero can also be prepared by reacting the substituted amine of formula VI and the aldehyde of formula VII with the dichlorophosphine of the formula R$_5$—CH$_2$PCl$_2$     (X)

to yield the intermediate of the formula

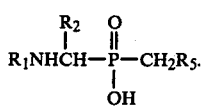
(XI)

The intermediate of formula XI is converted to the corresponding ester, i.e., R$_3$ is lower alkyl, benzyl, or phenethyl, as described above and then treated with lithium diisopropylamide and carbon dioxide to yield the acid of formula II wherein R$_3$ is lower alkyl, benzyl, or phenethyl.

The various imino acids and esters of formula III are described in the literature and in the various patents and pending U.S. application referred to above. Various substituted prolines are disclosed by Mauger et al., Chem. Review, Vo. 66, p 47–86 (1966). When the imino acid is known it can be readily converted to the ester by conventional means. For example, the esters where R$_6$ is t-butyl can be obtained by treating the corresponding N-carbobenzyloxyimino acid with isobutylene under acidic conditions and then removing the N-carbobenzyloxy protecting group by catalytic hydrogenation and the esters wherein R$_6$ is benzyl can be obtained by treating the imino acid with benzyl alcohol and thionyl chloride.

As disclosed by Krapcho in U.S. Ser. No. 164,985, now U.S. Pat. No. 4,316,905, the substituted prolines wherein R$_7$ is

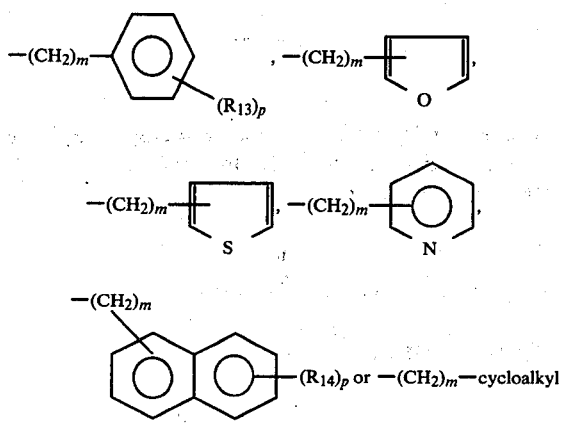

are prepared by reacting a 4-keto proline of the formula

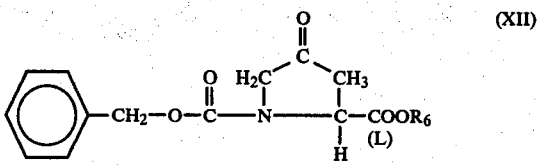
(XII)

with a solution of the Grignard or lithium reagent

R$_7$-Mg-halo or R$_7$-Li     (XIII)

wherein R$_7$ is as defined above and halo is Br or Cl to yield

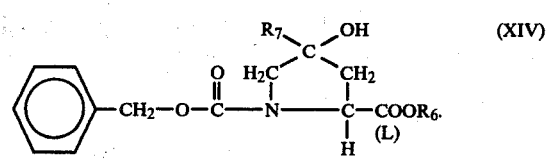
(XIV)

This compound is treated with a dehydrating agent such as p-toluenesulfonic acid, sulfuric acid, potassium bisulfate, or trifluoroacetic acid to yield the 3,4-dehydro-4-substituted proline of the formula

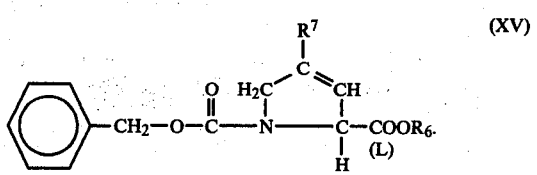
(XV)

Removal of the N-benzyloxycarbonyl protecting group and hydrogenation of the compound of formula XV yields the desired starting materials. The substituted proline wherein R$_7$ is cyclohexyl can be prepared by further hydrogenation of the 4-phenyl proline compound.

Preferred compounds of this invention with respect to the imino acid or ester part of the structure of formula I are those wherein: R$_6$ is hydrogen or

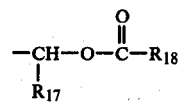

wherein

R$_{17}$ is hydrogen or methyl and R$_{18}$ is straight or branched chain lower alkyl of 1 to 4 carbons or phenyl.

R$_7$ is amino.

R$_7$ is hydrogen.

R$_7$ is hydroxy.

R$_7$ is chloro or fluoro.

R$_7$ is lower alkyl of 1 to 4 carbons or cyclohexyl.

R$_7$ is —O—lower alkyl wherein lower alkyl is straight or branched chain of 1 to 4 carbons.

R$_7$ is

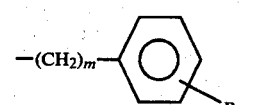

wherein m is zero, one or two, and $R_{13}$ is hydrogen, methyl, methoxy, methylthio, chloro, bromo, fluoro, or hydroxy.

$R_7$ is

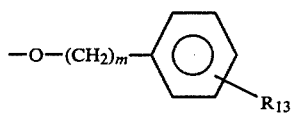

wherein m is zero, one or two, and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

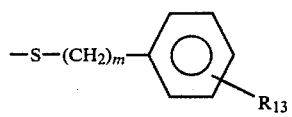

wherein m is zero, one or two, and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

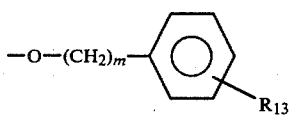

wherein m is zero, one or two, and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

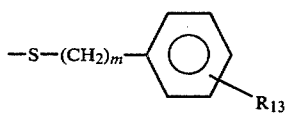

wherein m is zero, one or two, and $R_{13}$ is hydrogen, methyl, methoxy, methylthio, chloro, bromo, fluoro, or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or branched chain alkyl of 1 to 4 carbons or the $R_{16}$ groups join to complete an unsubstituted 5-or 6- membered ring or said ring in which one or more of the carbons has a methyl or dimethyl substituent.

$R_{11}$, $R_{11}'$, $R_{12}$ and $R_{12}'$ are all hydrogen, or $R_{11}$ is phenyl, 2-hydroxyphenyl or 4-hydroxyphenyl and $R_{11}'$, $R_{12}$ and $R_{12}'$ are hydrogen.

Most preferred compounds of this invention with respect to the imino acid or ester part of the structure of formula I are those wherein: X is

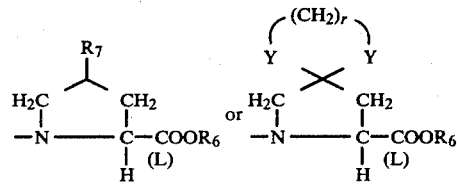

$R_6$ is hydrogen or

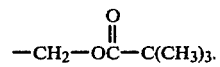

$R_7$ is hydrogen.
$R_7$ is cyclohexyl.
$R_7$ is lower alkoxy of 1 to 4 carbons.
$R_7$ is

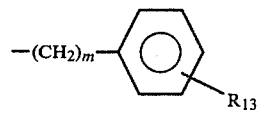

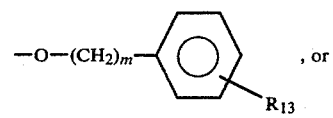

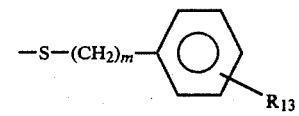

wherein m is zero, one, or two and $R_{13}$ is hydrogen, methyl, methoxy, methylthio, Cl, Br, F or hydroxy.

Y is oxygen or sulfur and r is two or three, especially wherein Y is sulfur and r is two.

Preferred compounds of this invention with respect to the phosphinylalkanoyl sidechain of the structure of formula I are those wherein:

$R_3$ is hydrogen or

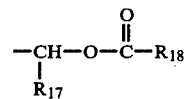

wherein $R_{17}$ is hydrogen or methyl and $R_{18}$ is straight or branched chain lower alkyl of 1 to 4 carbons or phenyl, especially hydrogen or

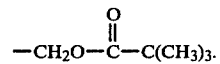

$R_1$ is hydrogen or

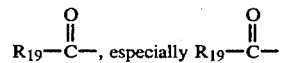

wherein $R_{19}$ is lower alkyl of 1 to 7 carbons; $CF_3$;

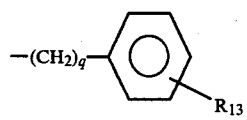

wherein q is zero or an integer from 1 to 4 and $R_{13}$ is hydrogen, methyl, methoxy, methylthio, chloro, bromo, fluoro, or hydroxy; cycloalkyl of 5 or 6 carbons;

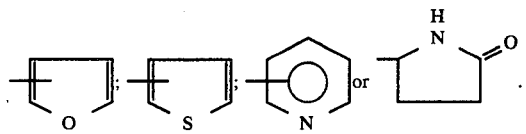

$R_5$ is hydrogen.
n is zero.
$R_2$ is lower alkyl of 1 to 7 carbons or

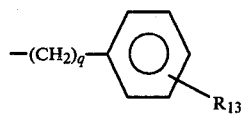

wherein q is zero or an integer from 1 to 4 and $R_{13}$ is hydrogen, methyl, methoxy, methylthio, chloro, bromo, fluoro or hydroxy; especially

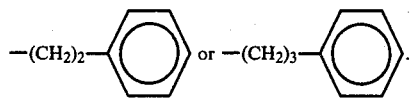

The compounds of this invention wherein at least one of $R_3$ or $R_6$ is hydrogen, form basic salts with various inorganic and organic bases which are also within the scope of the invention. Such salts include ammonium salts, alkali metal salts like lithium, sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

As shown above, the imino acid or ester portion of the molecule of the products of formula I is in the L-configuration. Depending upon the definitions of $R_2$ and $R_5$ one or two asymmetric centers may be present in the phosphinylalkanoyl sidechain. Thus, some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula III.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→ angiotensin I→ angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

(±)-1-[[(1-Amino-3-phenylpropyl)hydroxyphosphinyl]acetyl]-L-proline (a)

Methyl[3-phenyl-1-[[(phenylmethoxy)carbonyl]amino]propyl]phosphinic acid

Pivalic acid (4.08 g., 0.04 mole) and benzyl carbamate (3.02 g., 0.02 mole) are dissolved in 30 ml. of toluene. A portion of the toluene (5 ml.) is distilled at atmospheric pressure to remove traces of water. The solution is cooled to room temperature under argon, and methyldichlorophosphine (1.8 ml., 0.02 mole) and powdered 4 A° molecular sieves (2 g.) are added. 3-Phenylpropionaldehyde (3.3 ml., 0.025 mole) are then added dropwise over ten minutes. A slight exotherm (to approximately 35°) is observed. After stirring for one hour, the reaction mixture is poured into saturated sodium bicarbonate and extracted with dichloromethane. The aqueous solution is acidified to pH 3.5 with concentrated HCl and extracted with ether. The aqueous solution is then acidified to pH 1 and extracted with dichloromethane. The pH 1 extracts are dried (MgSO4) and evaporated to 2.1 g. of white solid product. The pH 3.5 extracts are dried (MgSO4) and evaporated (finally at 70°/1 mm. to remove pivalic acid) to yield an additional 3.2 g. of white solid product. Crystallization from ethyl acetate gives an analytical sample of methyl[3-phenyl-1-[[(phenylmethoxy)carbonyl]amino]propyl]phosphinic acid; m.p., 126°–129°.

Anal. Calc'd. for $C_{18}H_{22}NO_4P$: C, 62.24; H, 6.39; N, 4.03; P, 8.92. Found: C, 62.23; H, 6.52; N, 3.94.

Tlc (dichloromethane/acetic acid/methanol 8:1:1) $R_f=0.7$.

(b)

Methyl[3-phenyl-1-[[(phenylmethoxy)carbonyl]amino]propyl]phosphinic acid, phenylmethyl ester The product from part (a) (5.1 g., 0.0147 mole) is dissolved in dichloromethane and cooled to 0°. 1-Benzyl-3-p-tolyltriazine (3.4 g., 0.015 mole) in 75 ml. of dichloromethane is added dropwise. When gas evolution ceases, two additional portions (3.4 g. each) of the 1-benzyl-3-p-tolyltriazine are added and the mixture is stirred overnight. The solution is then washed with 5% potassium bisulfate, saturated sodium bicarbonate, and brine, dried (MgSO4), and evaporated to 11 g. of dark orange semi-solid. Chromatography on silica gel using dichloromethane ethyl acetate mixtures yields 4.0 g. of methyl[3-phenyl-1-[[(phenylmethoxy)carbonyl]amino]propyl]phosphinic acid, phenylmethyl ester as a pale yellow semi-solid. Tlc (ethyl acetate) $R_f=0.35, 0.4$.

(c)

[(Phenylmethoxy)[3-phenyl-1-[[(phenylmethoxy)carbonyl]amino]propyl]phosphinyl]acetic acid A solution of 0.04 moles of lithium diisopropylamide in tetrahydrofuran is prepared by the dropwise addition of N-butyllithium (16 ml. of 2.6 N solution, 0.04 mole) to a cooled (0°) solution of diisopropylamine (5 g., 0.05 mole) in pentane (75 ml.). The solvent is removed in vacuo and replaced by tetrahydrofuran (50 ml.). The solution is cooled to −76° and a solution of the phenylmethyl ester product from part (b) (3.8 g., 0.0084 mole) in tetrahydrofuran (50 ml.) is added over a period of thirty minutes. After stirring for fifteen minutes, carbon dioxide, dried over molecular sieves, is bubbled into the mixture for ten minutes. After stirring for ten minutes, and warming to room temperature, the solvent is removed in vacuo. The residue is acidified to pH of 1 with 10% hydrochloric acid and extracted with dichloromethane, washed with brine, and dried (MgSO4). The solvent is removed in vacuo. The oil residue is extracted into 10 ml. of 1 N sodium hydroxide plus 90 ml. of water and washed with dichloromethane/ethyl ether (1:1, 2×25 ml.). The alkaline phase is acidified to a pH of 1 with 10% hydrochloric acid. The oil separating from solution is extracted into dichloromethane, washed with brine, and dried (MgSO4). The solvent is removed in vacuo to give 3.3 g. of [(phenylmethoxy)[3-phenyl-1-[[(phenylmethoxy)carbonyl]amino]propyl]phosphinyl]acetic acid.

Tlc, silica gel, benzene/acetic acid (7:1) shows two spots, $R_f=0.17; 0.15$.

(d)

(±)-1-[[(Phenylmethoxy)[3-phenyl-1-[[(phenylmethoxy)carbonyl]amino]propyl]phosphinyl]acetyl]-L-proline, phenylmethyl ester 1,1-Carbonyldiimidazole (0.92 g., 0.0057 mole) is added to a chilled (0°) solution of the product from part (c) (2.75 g., 0.0057 mole) in acetonitrile (25 ml.). The mixture is stirred at 0° for one hour. A solution of L-proline, benzyl ester (1.2 g., 0.0057 mole) in acetonitrile (20 ml.) is added. After stirring at ambient temperature for 16 hours, the solvent is removed in vacuo. The residue is dissolved in dichloromethane (100 ml.), washed with 5% potassium bisulfate, saturated sodium bicarbonate, brine, and dried (MgSO4). The solvent is removed in vacuo. The residue (3.8 g.) is chromatographed on silica gel eluting with dichloromethane/ethyl acetate (1:1), followed by ethyl acetate, to give 2.2 g. of (±)-1-[[(phenylmethoxy)[3-phenyl-1-[[(phenylmethoxy)carbonyl]amino]propyl]phosphinyl]acetyl]-L-proline, phenylmethyl ester as a viscous oil.

(e)

(±)-1-[[(1-Amino-3-phenylpropyl)hydroxyphosphinyl]acetyl]-L-proline

A mixture of the L-proline,phenylmethyl ester product from part (d) (2.1 g., 0.0031 mole) and 5% palladium on carbon catalyst (100 mg.) in acetic acid/methanol (1:9, 50 ml.) is stirred vigorously under one atmosphere of hydrogen until the hydrogen is no longer consumed (216 ml.). The mixture is filtered through celite, and concentrated in vacuo. The residue is triturated with acetonitrile. The resulting solid in suspension is collected by filtration with a recovery of 1.1 g., m.p. 160°–190° (dec.). A portion (0.6 g.) is dissolved in double distilled water, millipore filtered, and lyophilized to yield 0.5 g. of (±)-1-[[(1-amino-3-phenylpropyl)hydroxyphosphinyl]acetyl]-L-proline, m.p. 160°–190° (dec.); $[\alpha]_D -43°$. Tlc, silica gel, butanol/acetic acid/water (3:1:1) shows a single spot, $R_f 0.44$.

Anal. Calc'd for $C_{16}H_{23}N_2O_5P$: 1 $H_2O$: C, 51.61; H, 6.76; N, 7.52; P, 8.32. Found: C, 51.79; H, 6.58; N, 7.46; P, 8.20.

EXAMPLE 2

(±)-1-[[(1-Aminopentyl)hydroxyphosphinyl]acetyl]-L-proline (a) Methyl[1-[[(phenylmethoxy)carbonyl]amino]pentyl]phosphinic acid Pivalic acid (4.08 g., 0.04 mole) is dissolved in 30 ml. of toluene. A portion (5 ml.) of toluene is distilled to remove traces of moisture, and the mixture is cooled to room temperature under argon. Benzyl carbamate (3.02 g., 0.02 mole), powdered 4 A° molecular sieves (2 g.) and methyldichlorophosphine (1.8 ml. 0.02 mole) are added. Valeraldehyde (2.7 ml., 0.025 mole) is added dropwise over 20 minutes, causing an exothermic reaction which raises the reaction temperature to 55°. After stirring one hour, the mixture solidifies. It is diluted with ether and filtered. The solid is crystallized from ethyl acetate to yield 3.4 g. of white solid product; m.p. 134°–135°. An additional 0.6 g. is obtained by concentrating the filtrate. Crystallization from ethyl acetate yields an analytical sample of methyl[1-[[(phenylmethoxy)carbonyl]amino]pentyl]phosphinic acid, m.p. 138°–150°.

Anal. Calc'd. for $C_{14}H_{22}NO_4P$: C, 56.18; H, 7.41; N, 4.68; P, 10.35. Found: C, 56.11; H, 7.61; N, 4.61; P, 10.4.

(b) Methyl[1-[[(phenylmethoxy)carbonyl]amino]pentyl]phosphinic acid, phenylmethyl ester The product from part (a) (4.0 g., 0.0134 mole) is dissolved in 300 ml. of dichloromethane and cooled in an ice bath. 1-Benzyl-3-p-tolyltriazene (8.4 g., 0.0373 mole) is added portionwise. After stirring overnight at room temperature, the solution is washed with 5% potassium bisulfate, saturated sodium bicarbonate, and brine, dried (MgSO$_4$) and evaporated to yield 11 g. of red oil. This material is chromatographed on silica gel using ethyl acetate to yield 5.1 g. of methyl[1-[[(phenylmethoxy)carbonyl]amino]pentyl]phosphinic acid, phenylmethyl ester as a white semi-solid.

(c) [(Phenylmethoxy)[1-[[(phenylmethoxy)carbonyl]amino]pentyl]phosphinyl]acetic acid A solution of 0.04 mole of lithium diisopropylamide in tetrahydrofuran is prepared by the dropwise addition of N-butyllithium (16 ml. of 2.6 N solution, 0.04 mole) to a cooled (0°) solution of diisopropylamine (5 g., 0.05 mole) in pentane (75 ml.). The solvent is removed in vacuo and replaced by tetrahydrofuran (50 ml.). The solution is cooled to −76° and a solution of the phenylmethyl ester product from part (b) (4.2 g., 0.0108 mole) in tetrahydrofuran (50 ml.) is added over a period of 30 minutes. After stirring for 15 minutes, carbon dioxide, dried over molecular sieves, is bubbled into the reaction mixture for 10 minutes. After stirring for 10 minutes, and warming to room temperature, the solvent is removed in vacuo. The residue is acidified to a pH of 1 with 10% hydrochloric acid and extracted with dichloromethane, washed with brine, and dried (MgSO$_4$). The solvent is removed in vacuo. The residue is dissolved in saturated sodium bicarbonate solution (75 ml.) and washed with dichloromethane. The alkaline phase is acidified to a pH of 1 with concentrated hydrochloric acid, extracted with dichloromethane, washed with brine, and dried (MgSO$_4$). The solvent is removed in vacuo to give 3.7 g. of [(phenylmethoxy)[1-[[(phenylmethoxy)carbonyl]amino]pentyl]phosphinyl]acetic acid as an oil. Tlc, silica gel, benzene/acetic acid (7:1): 2 spots, R$_f$0.17; 0.15.

(d) (±)-1-[[(Phenylmethoxy)[1-[[(phenylmethoxy)carbonyl]amino]pentyl]phosphinyl]acetyl]-L-proline, phenylmethyl ester 1,1-Carbonyldiimidazole (1.2 g., 0.0074 mole) is added to a chilled (0°) solution of the product from part (c) (3.2 g., 0.0074 mole) in acetonitrile (40 ml.). A solution of L-proline, benzyl ester (1.5 g., 0.0074 mole) in acetonitrile (20 ml.) is added. The mixture is stirred at ambient temperature for 16 hours. The solvent is removed in vacuo. The residue is dissolved in dichloromethane (100 ml.), washed with 5% potassium bisulfate, saturated sodium bicarbonate solution, brine, and dried (MgSO$_4$). The solution is concentrated in vacuo to give an oil residue of 4.8 g. Tlc, silica gel, ethyl acetate: major spot at R$_f$0.28, visualized with phosphomolybdic acid (PMA) and heat. It was chromatographed on silica gel, eluting with ethyl acetate/dichloromethane (1:1), and with ethyl acetate to give 3.2 g. of (±)-1-[[(phenylmethoxy)[1-[[(phenylmethoxy)carbonyl]amino]pentyl]phosphinyl]acetyl]-L-proline, phenylmethyl ester.

(e) (±)-1-[[(1-Aminopentyl)hydroxyphosphinyl]acetyl]-L-proline

A mixture of the phenylmethyl ester product from part (d) (3.1 g., 0.005 mole) and 5% palladium on carbon (150 mg.) in acetic acid/methanol [(1:9), 60 ml.] is stirred vigorously under one atmosphere of hydrogen until hydrogen is no longer consumed (about 350 ml.). The residue is triturated with acetonitrile to give a solid (1.5 g.) with an indefinite melting point (170°–190° dec.). Tlc, silica gel, butanol/acetic acid/water (3:1:1); single spot, R$_f$0.10, visualized with ninhydrin indicator. The solid is dissolved in water (120 ml.), washed with ethyl acetate, filtered, and lyophilized to give 1.4 g. of (±)-1-[[(1-aminopentyl)hydroxyphosphinyl]acetyl]-L-proline; m.p. 140°–190° (dec.); $[\alpha]_D$ −65°.

Anal. Calc'd. for $C_{12}H_{23}N_2O_5P \cdot 1H_2O$: C, 44.44; H, 7.45; N, 8.63; P, 9.55. Found: C, 44.73; H, 7.67; N, 8.66; P, 9.70.

EXAMPLE 3

(±)-1-[[(Aminoethyl)hydroxyphosphinyl]acetyl]-L-proline (a) Methyl [1-[[(phenylmethoxy)carbonyl]amino]ethyl]phosphinic acid Pivalic acid (10.2 g., 0.1 mole) is added to 100 ml. toluene. A portion of the toluene (10 ml.) is distilled to remove traces of moisture. Benzyl carbamate (7.5 g., 0.05 mole), powdered 4 A° molecular sieves (5.0 g.) and methyl dichlorophosphine (5.8 g., 0.05 mole) are added with stirring at room temperature. Acetaldehyde (3.3 g., 0.075 mole) is then added dropwise with vigorous stirring at ambient temperature over a period of 10 minutes. During the addition the temperature of the reaction mixture increases to 55°. After stirring for one hour, 100 ml. of dichloromethane is added and the mixture is filtered. The filtrate is concentrated in vacuo. The residue is dissolved in saturated sodium bicarbonate solution (125 ml.), washed with dichloromethane (3×40 ml.), and the combined dichloromethane wash is reextracted with saturated sodium bicarbonate solution (2×15 ml.). The combined aqueous alkaline phase is adjusted to a pH 3.2 with concentrated hydrochloric acid and extracted with ether (3×20 ml.). It is then acidified to a pH of 1 with concentrated hydrochloric acid and extracted with ethyl acetate (3×50 ml.), dried (MgSO4) and the solvent removed in vacuo. The residue (10.9 g.) solidifies at room temperature. Tlc, silica gel, dichloromethane/methanol/acetic acid (8:1:1) shows a major spot at $R_f$ 0.30. It is recrystallized from acetonitrile (110 ml.) to yield 8.7 g. of product. A second recrystallization from acetonitrile gives an analytically pure sample of methyl[1-[[(phenylmethoxy)carbonyl]amino]methyl]phosphinic acid; m.p. 118°–119°.

Anal. calc'd. for $C_{11}H_{16}NO_4P$: C, 51.36; H, 6.26; N, 5.45; P, 12.04. Found: C, 51.44; H, 6.36; N, 5.47; P, 11.76.

(b)
Methyl[1-[[(phenylmethoxy)carbonyl]amino]ethyl]-phosphinic acid, phenylmethyl ester A solution of the product from part (a) (9.2 g., 0.036 mole) in 150 ml. of dichloromethane is prepared by warming to reflux and then cooling to room temperature. Three equivalents of 3-benzyl-1-p-tolyltriazine is added portionwise with stirring. The mixture is stirred at ambient temperature overnight, washed with water, 5% potassium bisulfate, saturated sodium bicarbonate, dried (MgSO4) and evaporated in vacuo to give an oil residue. The residue is dissolved in ether (500 ml.). After refrigeration, a solid crystallizes from solution (7.6 g.); m.p. 108°–110°, partial melt, complete melt at 128°–130°. It is recrystallized from ethyl acetate (80 ml.) to yield 6.2 g. of product; m.p. 138°–140°, sintering 98°–108°. Recrystallization from ethyl acetate a second time gives an analytical sample of methyl [1-[[(phenylmethoxy)carbonyl]amino]ethyl]phosphinic acid, phenylmethyl ester; m.p. 138°–140°. Tlc, silica gel, benzene/acetic acid (7:1) shows a major spot at $R_f$ 0.21, visualized with PMA plus heat.

Anal. calc'd. for $C_{18}H_{22}NO_4P$: C, 62.24; H, 6.38; N, 4.03; P, 8.91. Found: C, 62.33; H, 6.50; N, 4.00; P, 8.86.

(c)
[(Phenylmethoxy)[1-[[(phenylmethoxy)carbonyl]amino]ethyl]phosphinyl]acetic acid A solution of 0.04 moles of lithium diisopropylamide in 50 ml. of tetrahydrofuran is prepared as in Example 1 (c). The solution is cooled to −76° and the solution of the phenylmethyl ester product from part (b) (3.5 g., 0.01 mole) in tetrahydrofuran (100 ml.) is added over a period of 30 minutes. After stirring for 15 minutes, carbon dioxide, dried over molecular sieves, is bubbled into the reaction mixture for 10 minutes. After stirring for 10 minutes, and warming to room temperature, the solvent is removed in vacuo. The residue is acidified to a pH of 1 with 10% hydrochloric acid, extracted with dichloromethane (2×75 ml.) and dried (MgSO4). The solvent is removed in vacuo. The residue is dissolved in 75 ml. of saturated sodium bicarbonate solution and washed with dichloromethane. The aqueous alkaline solution is acidified to a pH of 1 with concentrated hydrochloric acid, extracted with dichloromethane, washed with brine, and dried (MgSO4). The solvent is removed in vacuo to give 3.1 g. of [(phenylmethoxy)[1-[[(phenylmethoxy)carbonyl]amino]ethyl]phosphinyl] acetic acid as an oil. Tlc, silica gel, benzene/acetic acid (7:1) shows a major spot at $R_f$ 0.17.

(d)
(±)-1-[[(Phenylmethoxy)[1-[[(phenylmethoxy)carbonyl]amino]ethyl]phosphinyl]acetyl]-L-proline, phenylmethyl ester 1,1'-Carbonyldiimidazole (1 g. 0.066 mole) is added to a chilled (0°) solution of the product from part (c) (2.5 g., 0.063 mole) in 40 ml. of acetonitrile. The mixture is stirred for one hour at 0°. A solution of L-proline, benzyl ester (1.3 g., 0.066 mole) in 20 ml. of acetonitrile is added. The mixture is stirred at ambient temperature for 16 hours. The solvent is removed in vacuo. The residue is dissolved in dichloromethane (125 ml.), washed with 5% potassium bisulfate, saturated sodium bicarbonate solution, brine, and dried (MgSO4). The solution is concentrated in vacuo to give an oil residue of 3.3 g. Tlc, silica gel, ethyl acetate shows a major spot at $R_f$ 0.10. A portion (2.2 g.) is chromatographed on silica gel, eluting with ethyl acetate to give 1.7 g. of (±)-1-[(phenylmethoxy)[1-[[(phenylmethoxy)carbonyl]amino]ethyl]phosphinyl]acetyl]-L-proline, phenylmethyl ester.

(e)
(±)-1-[[(Aminoethyl)hydroxyphosphinyl]acetyl]-L-proline

A mixture of the product from part (d) (1.5 g., 0.0026 mole) and 5% palladium on carbon (100 mg.) in acetic acid/methanol [(1:9), 50 ml.] is stirred vigorously under one atmosphere of hydrogen until hydrogen absorption ceases (about 165 ml.). The mixture is filtered and concentrated in vacuo. The residue is dissolved in distilled water, millipore filtered, and lyophilized to give 0.65 g. of solid with an indefinite melting point, decomposing at 175°–200°. Tlc, silica gel, butanol/acetic acid/water (3:1:1) shows a single spot at $R_f$ 0.10, visualized with ninhydrin indicator. A solution of the combined product of two preparations (0.8 g.) in water (2 ml.) is placed on an AG-50 W column (1", 75 ml.) and eluted with water. The aqueous solution is lyophilized to give 0.7 g. of (±)-1-[[(aminoethyl)hydroxyphosphinyl]acetyl]-L-proline; m.p. 175°–200° (dec.). Tlc, silica gel, butanol/acetic acid/water (3:1:1) shows a single spot at $R_f$ 0.13, visualized with ninhydrin.

Anal. calc'd for: $C_9H_{17}N_2O_5P \cdot 0.5 H_2O$: C, 39.56; H, 6.64; N, 10.25; P, 11.33. Found: C, 39.22; H, 6.96; N, 10.16; P, 11.24.

EXAMPLES 4–17

Following the procedure of Examples 1 to 3 but coupling the phosphinylalkanoyl compound of formula I with L-proline, benzyl ester yields the intermediate of formula II. Removal of the protecting groups yields the product of formula III.

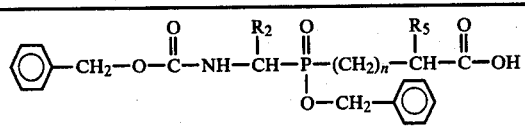
(I)
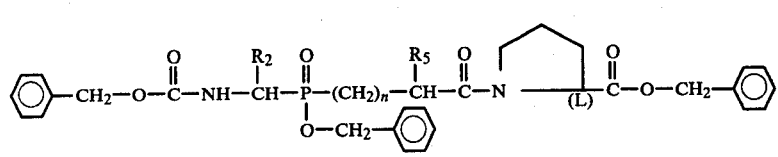
(II)
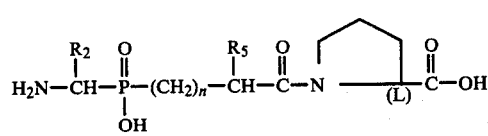
(III)
| Example | n | R₂ | R₅ |
|---|---|---|---|
| 4 | one | $-(CH_2)_2-C_6H_5$ | $-H$ |
| 5 | zero | $-(CH_2)_2-C_6H_5$ | $-CH_3$ |
| 6 | one | $-(CH_2)_2-C_6H_5$ | $-CF_3$ |
| 7 | zero | $-(CH_2)_2-C_6H_5$ | $-CH_2-C_6H_5$ |
| 8 | one | $-CH_2-C_6H_5$ | $-H$ |
| 9 | zero | $-H$ | $-(CH_2)_2-C_6H_5$ |
| 10 | one | $-CH_2-CH=CH_2$ | $-H$ |
| 11 | zero | $-CH_2CCl_3$ | $-H$ |
| 12 | zero | $-(CH_2)_2$-(2-thienyl) | $-H$ |
| 13 | zero | $-(CH_2)_2$-(2-furyl) | $-H$ |
| 14 | zero | $-(CH_2)_2$-(pyridyl) | $-H$ |
| 15 | zero | $-C_6H_5$ | $-CH_3$ |
| 16 | zero | $-(CH_2)_2-C_6H_4-OCH_3$ | $-H$ |
| 17 | one | $-(CH_2)_2-C_6H_4-F$ | $-H$ |

EXAMPLE 18

(±)-1-[[[1-[(Ethoxycarbonyl)amino]-3-phenylpropyl]-hydroxyphosphinyl]acetyl]-L-proline (a) Methyl [1-[(ethoxycarbonyl)amino]-3-phenylpropyl]phosphinic acid Pivalic acid (10.2 g., 1 mole) and urethan (4.5 g., 0.05 mole) are dissolved in 160 ml. of toluene. A portion of the toluene (10 ml.) is distilled at atmospheric pressure to remove traces of water. The solution is cooled to room temperature under argon and methyldichlorophosphine (5.6 g., 0.05 mole) and powdered 4 A° molecular sieves (5 g.) are added, followed by hydrocinnamaldehyde (8 g., 0.06 mole) via syringe. A slight exotherm (to approximately 43°) is observed. After stirring one hour the solids in suspension are removed by filtration. The filtrate is concentrated in vacuo. The residue is triturated with diisopropylether (50 ml.) to give 12.1 g. of solid product; m.p. 119°–125°. Tlc, silica gel, butanol/acetic acid/water (3:1:1) shows a major spot at $R_f$ 0.50, plus a minor spot at $R_f$ 0.55 visualized with PMA plus heat. A sample is recrystallized from ethyl acetate (10 ml.) to yield 0.3 g. of methyl [1-[(ethoxycarbonyl)amino]-3-phenylpropyl]phosphinic acid; m.p. 127°–129°.

Anal. Calc'd. for $C_{13}H_{20}NO_4P$: C, 54.73; H, 7.06; N, 4.91; P, 10.85. Found: C, 54.79; H, 7.31; N, 4.62; P, 10.70.

(b) Methyl[1-[(ethoxycarbonyl)amino]-3-phenylpropyl]-phosphinic acid, phenylmethyl ester Bis (trimethylsilyl)acetamide (11 ml., 0.045 mole) is added via syringe to a solution of the product from part (a) (10 g., 0.035 mole) in dichloromethane (50 ml.) in an atmosphere of argon. The mixture is stirred at ambient temperature for one hour. The solvent and excess bis(trimethylsilyl)acetamide are removed in vacuo at room temperature. After the addition of dichloromethane (50 ml.) to the residue, phosphorous pentachloride (8.5 g. 0.04 mole) is added and the resulting solution is stirred for one hour. After removal of the solvent in vacuo at room temperature, dichloromethane (50 ml.) is added to the residue. The resulting solution is stirred at ambient temperature during the dropwise addition of a solution of benzyl alcohol (4.2 g., 0.039 mole) and triethylamine (5 g., 0.05 mole) in dichloromethane (20 ml.). After stirring 16 hours at room temperature, the reaction mixture is diluted to twice its volume with dichloromethane. After washing with brine, followed by saturated sodium bicarbonate, followed by brine, and drying (MgSO₄), the solvent is removed in vacuo. The residue is dissolved in ether and washed with water to a negative CL⁻ test. The solvent is removed in vacuo to give recovery of the product (11 g.) as an oil. Tlc, silica gel, ethyl acetate, shows a major spot at $R_f$ 0.40, plus a minor spot at origin (PMA visualization). Trituration of the oil with diisopropyl ether results in the separation of a solid (2.3 g., m.p. 124°–127°). Tlc, silica gel, ethyl acetate, shows one spot, $R_f$ 0.40. The filtrate is concentrated in vacuo to give recovery of an oil (8.1 g.). A portion of the solid (400 mg.) is recrystallized from benzene to yield 150 mg. of methyl [1-[(ethoxycarbonyl)amino]-3-phenylpropyl]phosphinic acid, phenylmethyl ester; m.p. 128°–130°.

Anal. calc'd. for $C_{20}H_{26}NO_4P$: C, 63.99; H, 6.98; N, 3.73; P, 8.25. Found: C, 64.04; H, 6.97; N, 3.54; P, 8.40.

(c) [(Phenylmethoxy)[1-[(ethoxycarbonyl)amino]-3-phenylpropyl]phosphinyl]acetic acid A solution of 0.09 mole of lithium diisopropylamide in 150 ml. of tetrahydrofuran, prepared according to the procedure of Example 1(c), is cooled to −76° and a solution of the phenylmethyl ester product from part (b) (10 g., 0.026 mole) in 40 ml. of tetrahydrofuran is added over a period of one hour. After stirring for 15 minutes, carbon dioxide, dried over molecular sieves, is bubbled into the reaction mixture for 10 minutes. After stirring for 10 minutes, and warming to room temperature, the solvent is removed in vacuo. After the addition of water (50 ml.), the residue is acidified to a pH of 1 with concentrated hydrochloric acid. The oil that separates from solution is extracted into dichloromethane (200 ml.), washed with brine, and dried (MgSO₄). The solvent is removed in vacuo. The residue is dissolved in 5% sodium bicarbonate solution (100 ml.) and washed with ether (2×75 ml.). The alkaline aqueous solution is acidified to a pH of 1 with concentrated hydrochloric acid, extracted with dichloromethane, washed with brine, and dried (MgSO₄). The solvent is removed in vacuo. The semi-solid residue (8.6 g.) is recrystallized from ethyl acetate (100 ml.) to yield 4.8 g. of [(phenylmethoxy)[1-[(ethoxycarbonyl)amino]-3-phenylpropyl]phosphinyl]acetic acid; m.p. 151°–153°. Tlc, butanol/acetic acid/water (3:1:1) shows a single spot, $R_f$ 0.70 visualized with PMA plus heat.

Anal. Calc'd. for $C_{21}H_{26}NO_6P$: C, 60.14; H, 6.25; N, 3.34; P, 7.38. Found: C, 59.88; H, 6.17; N, 3.13; P, 7.19.

(d) (±)-1-[[(Phenylmethoxy)[1-[(ethoxycarbonyl)amino]-3-phenylpropyl]phosphinyl]acetyl]-L-proline, phenylmethyl ester 1,1-Carbonyldiimidazole (1.8 g., 0.011 mole) is added to a chilled (0°) solution of the product from part (c) (4.6 g., 0.011 mole) in 50 ml. of acetonitrile. The mixture is stirred for one hour at 0° and a solution of L-proline, benzyl ester (2.3 g., 0.011 mole) in 25 ml. of acetonitrile is added. The mixture is stirred at ambient temperature for 16 hours. The solvent is removed in vacuo. The residue is dissolved in 200 ml. of dichloromethane, washed with 5% potassium bisulfate, saturated sodium bicarbonate solution, brine, and dried (MgSO₄). The solvent is removed in vacuo to give an oil residue of 6.5 g. Tlc, silica gel, ethyl acetate, shows a major spot at $R_f$ 0.50 visualized with PMA. The residue is chromatographed on silica gel, eluted with dichloromethane/ethyl acetate (9:1) and (4:1) to give 5.4 g. of (±)-1-[(phenylmethoxy)[1-[(ethoxycarbonyl)amino]-3-phenylpropyl]phosphinyl]acetyl]-L-proline, phenylmethyl ester. Tlc shows a single spot at $R_f$ 0.50.

(e) (±)-1-[[[1-[(Ethoxycarbonyl)amino]-3-phenylpropyl]-hydroxyphosphinyl]acetyl]-L-proline A mixture of the product from part (d) (5.2 g., 0.088 mole) and 5% palladium on carbon (200 mg.) in methanol (65 ml.) plus 1 ml. of glacial acetic acid is stirred vigorously under one atmosphere of hydrogen until hydrogen absorption ceases (about 400 ml.). The mixture is filtered and concentrated in vacuo. Tlc, silica gel, butanol/acetic acid/water (3:1:1) of the residue (3.4 g.)

shows a major spot at $R_f$ 0.46 and a minor spot at 0.50 (visualized with PMA). A portion of the residue (0.3 g., 0.0007 mole) is chromatographed on a column of DEAE Sephadex ($NH_4^-$ form) (100 ml.—15 mm diameter column) and eluted with a gradient of 0.005 m to 0.5 m ammonium bicarbonate solution. The UV positive fractions are collected, millipore filtered, and lyophilized to give a residue of 0.3 g. Tlc shows a major spot at $R_f$ 0.46 and a shadow at $R_f$ 0.50. The residue is dissolved in 3–4 ml. of double distilled water and placed on a column of AG 50-W resin ($H^+$ form) (30 ml.) and eluted with water. The acidic fractions are collected, millipore filtered, and lyophilized to give 168 mg. of (±)-1-[[[1-[(ethoxycarbonyl)amino]-3-phenylpropyl]hydroxyphosphinyl]acetyl]-L-proline.

Anal. calc'd. for $C_{19}H_{27}N_2O_7P \cdot H_2O$: C, 51.34; H, 6.57; N, 6.30; P, 6.97. Found: C, 51.17; H, 6.35; N, 6.26; P, 6.81.

EXAMPLE 19

(±)-1-[[Hydroxy[3-phenyl-1-[(trifluoroacetyl)amino]propyl]phosphinyl]acetyl]-L-proline, dilithium salt (a) Methyl(1-amino-3-phenylpropyl)phosphinic acid, hydrochloride A suspension of methyl [1-[(ethoxycarbonyl)amino]-3-phenylpropyl]phosphinic acid from Example 18(a) (9.8 g., 0.034 mole) in 22.2% hydrochloric acid (200 ml.) is heated at reflux for 24 hours. After filtration, the resulting solution is concentrated in vacuo. Water (100 ml.) is added to the residue and the solution is again concentrated in vacuo. Trituration of the residue with refluxing acetonitrile (125 ml.) results in the separation of solid product (7.5 g.); m.p. 196°–200° (dec.). A portion (0.4 g.) is recrystallized from absolute ethanol (10 ml.) to yield 0.27 g. of an analytical sample of methyl(1-amino-3-phenylpropyl)phosphinic acid, hydrochloride; m.p. 198°–200° (dec.).

Anal. Calc'd. for $C_{10}H_{16}NO_2P \cdot HCl$: C, 48.10; H, 6.46; N, 5.61; Cl, 14.20; P, 12.41. Found: C, 47.98; H, 6.99; N, 5.56; Cl, 14.14; P, 12.10.

(b) Methyl [3-phenyl-1-[(trifuoroacetyl)amino]propyl]phosphinic acid

A mixture of the product from part (a) (7.5 g., 0.026 mole) and 25 ml. of trifluoroacetic anhydride is stirred at ambient temperature for two hours. The excess anhydride is removed in vacuo. The residue is triturated with refluxing diisopropyl ether (500 ml.) to give 7.5 g. of solid product; m.p. 138°–145°. Tlc, silica gel, butanol/acetic acid/water (3:1:1) shows one spot, $R_f$ 0.70. A portion (0.5 g.) is recrystallized from diisopropyl ether (800 ml.) to yield 0.4 g. of an analytical sample of methyl [3-phenyl-1-[(trifluoroacetyl)amino]propyl]phosphinic acid, m.p. 145°–145°.

Anal. calc'd. for $C_{12}H_{15}F_3NO_3P$: C, 46.61; H, 4.89; N, 4.53; F, 18.43; P, 10.02. Found: C, 46.41; H, 4.83; N, 4.46; F, 18.15; P, 9.89.

(c) Methyl[3-phenyl-1-[(trifluoroacetyl)amino]propyl]phosphinic acid, phenylmethyl ester Bis(trimethylsilyl)acetamide (8 ml., 0.033 mole) is added to a suspension of the product from part (b) (7 g., 0.023 mole) in 50 ml. of dichloromethane, in an atmosphere of argon. A solution of the solid occurs rapidly and the mixture is stirred at ambient temperature for one hour. The solvent and excess bis(trimethylsilyl)acetamide are removed in vacuo at room temperature. The residue is dissolved in 50 ml. of dichloromethane and phosphorous pentachloride (5.7 g., 0.027 mole) is added. After stirring for one hour, the solvent and excess pentachloride are removed in vacuo. The residue is dissolved in 50 ml. of dichloromethane and a solution of benzyl alcohol (2.8 g., 0.026 mole) and triethylamine (3.5 g., 0.034 mole) in 20 ml. of dichloromethane is added dropwise with stirring. After stirring at ambient temperature for 16 hours, the mixture is diluted to twice its volume with dichloromethane. The solution is washed with 5% potassium bisulfate, water, brine, and dried ($MgSO_4$). After concentrating in vacuo, the semisolid residue (8.7 g.) is triturated with 200 ml. of diisopropyl ether. A solid (2.4 g., m.p. 145°–155°) is collected by filtration (Tlc shows a single spot at $R_f$ 0.60). A portion of the solid product (0.3 g.) is recrystallized from 75 ml. of diisopropyl ether to yield 0.18 g. of an analytical sample of methyl[3-phenyl-1-[(trifluoroacetyl)amino]propyl]phosphinic acid, phenylmethyl ester; m.p. 165°–166°.

Anal. calc'd. for $C_{19}H_{21}F_3NO_3P$: C, 57.14; H, 5.30; N, 3.50; F, 14.27; P, 7.75. Found: C, 56.96; H, 5.32; N, 3.50; F, 13.99; P, 7.54.

(d) [(Phenylmethoxy)[3-phenyl-1-[(trifluoroacetyl)amino]propyl]phosphinyl]acetic acid A solution of 0.075 mole of lithium diisopropylamide in 150 ml. of tetrahydrofuran is prepared according to the procedure of Example 1(c) and cooled to −76°. A solution of the product from part (c) (8.4 g., 0.021 mole) in 40 ml. of tetrahydrofuran is added over a period of 50 minutes. After stirring for 15 minutes, carbon dioxide, dried over molecular sieves, is bubbled into the reaction mixture for 10 minutes. After stirring for 10 minutes, and warming to room temperature, the solvent is removed in vacuo. After the addition of 10% hydrochloric acid (50 ml.) to the residue, with cooling, concentrated hydrochloric acid is added to a pH of 1. The mixture is extracted with 300 ml. of dichloromethane, washed with brine, and dried ($MgSO_4$). The solvent is removed in vacuo. Tlc, silica gel, butanol/acetic acid/water (3:1:1) of the residual oil (8.5 g.) shows a major spot at $R_f$ 0.70. The material is chromatographed on silica gel, eluting with toluene/acetic acid (9:1) to give 6.1 g. of [(phenylmethoxy)[3-phenyl-1-[(trifluoroacetyl)amino]propyl]phosphinyl]-acetic acid. Tlc shows a single spot at $R_f$ 0.70.

(e) (±)-1-[[(Phenylmethoxy)[3-phenyl-1-[(trifluoroacetyl)amino]propyl]phosphinyl]acetyl]-L-proline, phenylmethyl ester 1,1-Carbonyldiimidazole (2.2 g., 0.0133 mole) is added to a chilled (0°) solution of the product from part (d) (5.9 g., 0.0133 mole) in 50 ml. of acetonitrile. The mixture is stirred for one hour at 0° and a solution of L-proline, benzyl ester (2.7 g., 0.0133 mole) in 20 ml. of acetonitrile is added. The mixture is stirred at ambient temperature for 16 hours. The solvent is removed in vacuo. The residue is dissolved in 200 ml. of dichloromethane, washed with 5% potassium bisulfate solution, brine, and dried ($MgSO_4$). The solution is concentrated in vacuo to give a syrupy residue of 8.2 g. Tlc, silica gel, ethyl acetate/dichloromethane (1:4) shows a major spot at $R_f$ 0.40 with 3 minor additional spots, including one at origin (visualized with PMA plus heat). The residue is chromatographed on silica gel, eluting with ethyl acetate/dichloromethane (1:9) to give two fractions, Tlc of one fraction (1.9 g.) shows a single spot at $R_f$ 0.40; the other fraction (4.5 g.) shows two spots, a major one at $R_f$ 0.40 plus a minor at $R_f$ 0.35. The chromatographically pure (±)-1-[[(phenylmethoxy)[3-phenyl-1-[(trifluoroacetyl)amino]propyl]phosphinyl]acetyl]-L-proline, phenylmethyl ester is employed in the following steps.

(f)
(±)-1-[[Hydroxy[3-phenyl-1-[(trifluoroacetyl)amino]propyl]phosphinyl]acetyl]-L-proline A mixture of the product from part (e) (1.6 g., 0.0025 mole) and 10% palladium on carbon (0.1 g.) in 50 ml. of ethyl acetate is stirred vigorously in an atmosphere of hydrogen until absorption of hydrogen ceases (about 113 ml. of hydrogen). The mixture is filtered and concentrated in vacuo to give 1.1 g. Tlc, silica gel, dichloromethane/methanol/acetic acid (8:1:1) shows a major spot at $R_f$ 0.22 and a minor spot at $R_f$ 0.04 ($I_2$ visualization). A solution of water insoluble residue (a glassy solid) is effected in methanol (1.0 g., 0.0022 mole to 4 ml.) plus water (2 ml.) and placed on a column of DEAE Sephadex ($NH_4HCO_3$, 200 ml.) and eluted with a gradient of 0.005 mole to 0.5 mole ammonium bicarbonate solution. The UV positive fractions are collected, millipore filtered, and lyophilized to give 1.1 g. The solid is dissolved in 5 ml. of water, placed on a column of AG-50 W (H+) (75 ml.), and eluted with water. The acidic fractions are collected, millipore filtered, and lyophilized to give 0.9 g. of (±)-1-[[hydroxy[3-phenyl-1-[(trifluoroacetyl)amino]propyl]phosphinyl]acetyl]-L-proline as a glass-like solid. Tlc, silica gel, butanol/acetic acid/water (3:1:1) shows a single spot at $R_f$ 0.50 (visualized with PMA plus heat).

(g)
(±)-1-[[Hydroxy[3-phenyl-1-[(trifluoroacetyl)amino]propyl]phosphinyl]acetyl]-L-proline, dilithium salt A solution of the product from part (f) (0.9 g., 0.002 mole) in water is effected by the addition of one equivalent (2 ml.) of 1 N lithium hydroxide plus 2 ml. of water. The solution is placed on a column of AG-50 W (Li+) (75 ml.) and eluted with water. The acidic fractions (pH 4–5.5) are collected, millipore filtered, and lyophilized to give 0.9 g. of (±)-1-[[hydroxy[3-phenyl-1-[(trifluoroacetyl)amino]propyl]phosphinyl]acetyl]-L-proline, dilithium salt. Tlc, silica gel, ethyl acetate, butanol/acetic acid/water (3:1:1) shows a single spot at $R_f$ 0.50.

Anal. Calc'd. for $C_{18}H_{20}F_3N_2O_6P \cdot 2Li \cdot 1.25H_2O$: C, 44.60; H, 4.68; N, 5.78; F, 11.76; P, 6.39. Found: C, 44.53; H, 4.56; N, 5.82; F, 11.93; P, 6.60.

EXAMPLE 20

(±)-1-[[[1-(Benzoylamino)-4-phenylbutyl]hydroxyphosphinyl]acetyl]-L-proline (a) Carbomethoxymethyldichlorophosphine Ketene is passed through a solution of tributyltin methoxide (64 g., 0.199 mole) in 200 ml. of anhydrous ether at 0° until Tlc (silica gel, methanol:dichloromethane; 1:9) indicates complete consumption of starting material ($R_f$ equals 0.14). The ether is removed in vacuo and the residue distilled to give 62.75 g. of carbomethoxymethyl tributyltin as a pale yellow liquid; b.p. 117°–120° (0.8 mm Hg).

A mixture of carbomethoxymethyl tributyltin (80 g., 0.22 mole) and phosphorus trichloride (80 ml., 0.92 mole) is treated with 2,2'-azobisisobutyronitrile (230 mg., 1.4 mmole) and slowly heated to reflux under argon. After refluxing for 30 minutes, the excess phosphorus trichloride is distilled off under reduced pressure. Distillation of the residue gives carbomethoxymethyldichlorophosphine as a colorless liquid; b.p. 52° (2 mm of Hg).

(b)
[[4-Phenyl-1-[[(phenylmethoxy)carbonyl]amino]butyl]hydroxyphosphinyl]acetic acid, methyl ester A mixture of pivalic acid (5.5 g., 0.054 mole) and benzyl carbamate (4.1 g., 0.027 mole) in 100 ml. of toluene is heated to reflux and a portion of the toluene (10 ml.) is removed by distillation at atmospheric pressure to remove traces of water. The solution is cooled to room temperature, under argon, and powdered 4 A° molecular sieves (5 g.) are added, followed by the addition of carbomethoxymethyldichlorophosphine (4.7 g., 0.027 mole) from part (a). 4-Phenylbutyraldehyde (4.4 g., 0.03 mole), prepared according to the procedure in Tetrahedron, Vol. 34, p. 1651 (1978), is added dropwise over five minutes via syringe. A slight exotherm (approximately 38°) is observed. The mixture is stirred at ambient temperature for 16 hours. After filtration and concentration in vacuo, 200 ml. of water is added to the residue followed by the addition of saturated sodium bicarbonate solution to a pH of 8–9. The alkaline aqueous phase is washed with ether and acidified to a pH of 1–2 with concentrated hydrochloric acid. The oil that separated from solution is extracted into ethyl acetate, washed with brine, and dried ($MgSO_4$). After concentrating in vacuo, the residue is triturated with diisopropyl ether to yield 5 g. of product. Tlc, silica gel, dichloromethane/methanol/acetic acid (8:1:1) shows a major spot at $R_f$ 0.56 plus a minor spot at $R_f$ 0.10, and a shadow at $R_f$ 0.70. The material is recrystallized from toluene (30 ml.) to yield 4 g. [[4-phenyl-1-[[(phenylmethoxy)carbonyl]amino]butyl]hydroxyphosphinyl]acetic acid, methyl ester; m.p. 107°–109°. Tlc shows a single spot at $R_f$ 0.56, with a shadow at $R_f$ 0.08.

Anal. calc'd. for $C_{21}H_{26}NO_6P$: C, 60.12; H, 6.27; N, 3.33; P, 7.38. Found: C, 59.89; H, 6.18; N, 3.23; P, 7.40.

(c)
[[1-(Amino)-4-phenylbutyl]hydroxyphosphinyl]acetic acid

A suspension of the product from part (b) (2.8 g., 0.0067 moles) in 10% hydrochloric acid (60 ml.) is stirred at reflux until Tlc shows the absence of starting material (about three hours). The mixture is washed with ether and concentrated in vacuo. The residue is repeatedly treated with water (20 ml.) and concentrated in vacuo until a white solid separates when water is added to the residue. After cooling in an ice-water bath, the solid is collected by suction-filtration and dried in vacuo to give 1.05 g. [[1-(amino)-4-phenylbutyl]hydroxyphosphinyl]acetic acid; m.p. 189°–190° (dec.).

Anal. calc'd. for $C_{12}H_{18}NO_4P$: C, 53.13; H, 6.69; N, 5.16; P, 11.42. Found: C, 53.54; H, 6.41; N, 5.08; P, 11.20.

(d)

[[1-(Benzoylamino)-4-phenylbutyl]hydroxyphosphinyl]acetic acid

To a suspension of the product from part (c) (1 g., 0.0037 mole) in water (30 ml., pH 2.3), solid sodium carbonate is added until solution is effected (pH 8.5). The pH of the solution is maintained at a pH of 8.5-9 by the addition of solid sodium bicarbonate during the dropwise addition of a solution of benzoyl chloride (0.52 g., 0.0037 mole) in 5 ml. of acetone. After the addition is completed an additional equivalent of benzoyl chloride is added dropwise (0.5 g. in 5 ml. of acetone), while maintaining the pH at 8.5-9 by the addition of sodium bicarbonate. The alkaline solution is washed with ether, acidified to a pH of 1 with concentrated hydrochloric acid, and the oil that separates is extracted into ethyl acetate, washed with brine, and dried (MgSO$_4$). The solvent is removed in vacuo and the residue is triturated with diisopropyl ether to give 1.4 g. of solid [[1-(benzoylamino)-4-phenylbutyl]hydroxyphosphinyl]acetic acid; m.p. 170°-175° (turbid melt). Tlc, silica gel, butanol/acetic acid/water (3:1:1), shows a single spot at R$_f$ 0.50.

(e)

(±)-1-[[[1-(Benzoylamino)-4-phenylbutyl]hydroxyphosphinyl]acetyl]-L-proline, phenylmethyl ester 1,1-Carbonyldiimidazole (0.36 g., 0.0022 mole) is added to a solution of the product from part (d) (0.75 g., 0.002 mole) in acetonitrile/tetrahydrofuran (1:1, 40 ml.), cooled in an ice/water bath. The mixture is stirred in the cold for one hour and followed by the addition of L-proline, benzyl ester (0.45 g., 0.0022 mole) in 5 ml. of tetrahydrofuran. After stirring at ambient temperature for 16 hours, the mixture is concentrated in vacuo. The residue is dissolved in ethyl acetate (100 ml.) plus water (10 ml.) and washed to a pH of 2 with 5% potassium bisulfate, brine, and dried (MgSO$_4$). The solution is concentrated in vacuo to give a glass-like residue. Tlc, silica gel, dichloromethane/acetic acid/water (8:1:1), shows a major, elongated spot at R$_f$ 0.75, plus a minor spot at R$_f$ 0.10 and several faster moving spots. The residue is chromatographed on silica gel, eluted with dichloromethane/methanol/acetic acic (15:1:1) to give 0.7 g. of (±)-1-[[[1-(benzoylamino)-4-phenylbutyl]hydroxyphosphinyl]acetyl]-L-proline, phenylmethyl ester. Tlc shows a single spot at R$_f$ 0.75.

(f)

(±)-1-[[[1-(Benzoylamino)-4-phenylbutyl]hydroxyphosphinyl]acetyl]-L-proline

A mixture of the product from part (e) (0.67 g., 0.0012 mole) and 10% palladium on carbon catalyst (50 mg.) in methanol/water (9:1) is stirred vigorously in an atmosphere of hydrogen at ambient temperature for 16 hours. Tlc shows reduction is incomplete and after filtration, fresh catalyst (50 mg.) is added and the mixture is stirred at an atmosphere of hydrogen for an additional 4 hours. Tlc shows the absence of starting material with a single elongated spot at R$_f$ 0.24. After filtration, the mixture is concentrated in vacuo. The residue is dissolved in dichloromethane and dried (MgSO$_4$). Removal of the solid gives 0.35 g. of (±)-1-[[[1-(benzoylamino)-4-phenylbutyl]hydroxyphosphinyl]acetyl]-L-proline as a gray colored solid. Tlc, silica gel, butanol/acetic acid/water (3:1:1), shows a single spot at R$_f$ 0.50.

Anal. calc'd. for C$_{24}$H$_{29}$N$_2$O$_6$P.2H$_2$O C, 56.68; H, 5.75; N, 5.51; P, 5.5. Found: C, 56.45; H, 5.88; N, 5.07; P, 5.9.

EXAMPLE 21

(±)-1-[[[1-(Benzoylamino)heptyl]hydroxyphosphinyl]acetyl]-L-proline

(a)

[[1-[[(Phenylmethoxy)carbonyl]amino]heptyl]hydroxyphosphinyl]acetic acid, methyl ester Pivalic acid (5.1 g., 0.05 mole) and benzylcarbamate (3.8 g., 0.025 mole) are dissolved in 100 ml. of toluene. A portion (10 ml.) of the toluene is removed by distillation at atmospheric pressure to remove traces of water. The solution is cooled, under argon, to room temperature, and powdered 4 A° molecular sieves (5 g.) are added, followed by the addition of carbomethoxymethyldichlorophosphine (prepared according to the procedure of Example 20 (a), 4.4 g., 0.025 mole). Freshly distilled heptaldehyde (3.4 g., 0.003 mole) is added dropwise via syringe to the above mixture, with stirring, at the rate of 1.7 ml./min. A slight exotherm (38°) is observed. The mixture is stirred at ambient temperature for 16 hours. The solids are removed by filtration. The filtrate is concentrated in vacuo. The residue is dissolved in 5% saturated sodium bicarbonate (50 ml.) plus water (50 ml.). The alkaline aqueous solution (pH 8) is washed with ether and acidified to a pH of 3.2 with concentrated hydrochloric acid. The oil that separates from solution is extracted into ether (2×150 ml.) and diluted to a volume of 300 ml. with ethyl acetate, washed with brine, and dried (MgSO$_4$). Solids are observed to crystallize from the ether/ethyl acetate mixture over the drying agent. After refrigeration overnight, the solids are collected and suspended in 200 ml. of water. The water insoluble solids are washed repeatedly with water to give 3.3 g. of [[1-[[(phenylmethoxy)carbonyl]amino]heptyl]hydroxyphosphinyl]acetic, methyl ester; m.p. 260°-268°, decomposition at 275°. Tlc, silica gel, benzene, acetic acid (7:3) shows a major spot at R$_f$ 0.20, with a minor spot at R$_f$ 0.30.

(b) [[1-(Amino)heptyl]hydroxyphosphinyl]acetic acid

A suspension of the product from part (a) (1.8 g., 0.0052 mole) in 10% hydrochloric acid (40 ml.) is stirred at reflux temperature until a turbid solution results and Tlc, silica gel, butanol/acetic acid/water shows the absence of starting material (about 6 hours). The mixture is cooled to room temperature, and washed with ether to remove an oil that separated from solution. The aqueous solution is concentrated in vacuo to give an oil residue. The procedure is repeated several times until the residue gives no positive chloride ion test and becomes semi-solid when triturated with ether. Finally, repeated trituration with refluxing acetonitrile gives 1.1 g. of solid [[1-(amino)heptyl]hydroxyphosphinyl]acetic acid; m.p. 180°-190°, gradual decomposition. Tlc, butanol/acetic acid/water (3:1:1) shows a single, ninhydrin sensitive spot at R$_f$ 0.49.

(c)

[[1-(Benzoylamino)heptyl]hydroxyphosphinyl]acetic acid

To a suspension of the product from part (b) (1 g., 0.004 mole) in 30 ml. of water, solid sodium carbonate is added portionwise until solution is effected (pH 9.5). A solution of benzoyl chloride (0.56 g., 0.004 mole) in 10 ml. of acetone is added dropwise to the above solution, while the pH is maintained at pH 9-9.5 by the addition of solid sodium carbonate. Following the addition and after stirring for 30 minutes, Tlc shows the presence of starting material. Additional benzoyl chloride (0.56 g., 0.004 mole) in 10 ml. of acetone is added and after stirring for 30 minutes, Tlc shows no ninhydrin sensitive product. After filtration and washing ether, the mixture is acidified to a pH of 1 with concentrated hydrochloric acid. The oil that separates from solution is extracted into ethyl acetate and dried (MgSO$_4$). The solvent is removed in vacuo and the semi-solid residue is triturated repeatedly with diisopropyl ether to give 0.6 g. of solid [[1-(benzoylamino)heptyl]hydroxyphosphinyl]acetic acid. Tlc, silica gel, butanol/acetic acid/water (3:1:1) shows a single spot at R$_f$ 0.50.

(d)
(±)-1-[[[1-(Benzoylamino)heptyl]hydroxyphosphinyl]acetyl]-L-proline, phenylmethyl ester 1,1'-Carbonyldiimidazole (0.32 g., 0.002 mole) is added to a chilled (0°) solution of the product from part (c) (0.58 g., 0.00154 mole) in 30 ml. of tetrahydrofuran. The mixture is stirred at 0° for one hour. A solution of L-proline, benzyl ester (0.4 g., 0.002 mole) in 5 ml. of tetrahydrofuran is added. After stirring at ambient temperature for 20 hours, the mixture is concentrated in vacuo. The residue is dissolved in ethyl acetate (50 ml.) and water (5 ml.), washed with 5% potassium bisulfate (to a pH of 2), brine, and dried (MgSO$_4$). The solvent is removed in vacuo to give a glass-like solid residue of 0.8 g. Tlc, silica gel, dichloromethane/methanol/acetic acid (19:1:1) shows a major spot at R$_f$ 0.14, plus a shadow at 0.33, and a single spot at origin. The solid is chromatographed on silica gel, eluted with dichloromethane/methanol (19:1) until Tlc shows no spot at R$_f$ 0.33, and finally eluted with dichloromethane/methanol/acetic acid (19:1:1) to give 0.66 g. of amorphous solid (±)-1-[[[1-(benzoylamino)heptyl]hydroxyphosphinyl]acetyl]-L-proline, phenylmethyl ester. Tlc shows a single spot at R$_f$ 0.14.

(e)
(±)-1-[[[1-(Benzoylamino)heptyl]hydroxyphosphinyl]acetyl]-L-proline

A mixture of the product from part (d) (0.6 g., 0.0011 mole) and 10% palladium on carbon catalyst (80 mg.) in methanol/water (95:5) is stirred vigorously in one atmosphere of hydrogen at ambient temperature, until hydrogen is no longer consumed (about 6 hours). After concentrating in vacuo, the residue is triturated with ether and collected by filtration to give 0.38 g. of amorphous solid (±)-1-[[[1-(benzoylamino)heptyl]hydroxyphosphinyl]acetyl]-L-proline; m.p. 260°-275° (dec.).

Anal. calc'd. for C$_{21}$H$_{31}$N$_2$O$_6$P.2.5H$_2$O: C, 52.16; H, 6.46; N, 5.79; P, 6.40. Found: C, 51.94; H, 6.08; N, 5.64; P, 6.20.

EXAMPLE 22

(±)-1-[[[1-(Benzoylamino)-3-phenylpropyl]hydroxyphosphinyl]acetyl]-4-[ethylenebis(thio)]-L-proline (a)
[[3-Phenyl-1-[[(phenylmethoxy)carbonyl]amino]propyl]hydroxyphosphinyl]acetic acid, methyl ester Pivalic acid (10.2 g., 0.1 mole) and benzyl carbamate (7.6 g., 0.05 mole) are dissolved in toluene (100 ml.). A portion of the toluene (20 ml.) is distilled at atmospheric pressure to remove traces of water. The solution is cooled to room temperature, under argon, and powdered 4 A° molecular sieves (10 g.) are added, followed by the addition of carbomethoxymethyldichlorophosphine (prepared according to Example 20 (a), 8.75 g., 0.05 mole). 3-Phenylpropionaldehyde (6.9 g., 0.05 mole) is then added dropwise over 5 minutes, a slight exotherm (approximately 45°) is observed. The reaction mixture is stirred at ambient temperature for one hour; after 30 minutes additional solids separate from the mixture resulting in the formation of a jelly that is stirred with difficulty. The solids are collected by filtration and extracted with refluxing dichloromethane (700 ml.). The dichloromethane solution is concentrated in vacuo. The residue is triturated with diisopropyl ether to give 11.6 g. of solid; m.p. 143°-147°. Tlc, silica gel, dichloromethane/methanol/acetic acid (8:1:1) shows a single spot at R$_f$ 0.50. A sample (0.4 g.) is recrystallized from ethyl acetate (20 ml.) to give an analytical sample of 0.35 g. of [[3-phenyl-1-[[(phenylmethoxy)carbonyl]amino]propyl]hydroxyphosphinyl]acetic acid, methyl ester; m.p. 147°-149°.

Anal. calc'd. for C$_{20}$H$_{24}$NO$_6$P: C, 59.25; H, 5.96; N, 3.45; P, 7.64. Found: C, 59.36; H, 6.10; N, 3.36; P, 7.50.

(b)
[[1-(Amino)-3-phenylpropyl]hydroxyphosphinyl]acetic acid

A suspension of the product from part (a) (3 g., 0.0074 mole) in 10% hydrochloric acid (60 ml.) is stirred at reflux until Tlc, silica gel, dichloromethane/methanol/acetic acid (8:1:1) shows the absence of starting material, and an elongated, ninhydrin sensitive, spot from origin to R$_f$ 0.20. The mixture is cooled to room temperature, washed with ether, and concentrated in vacuo. The residue is repeatedly treated with water (20 ml.) and concentrated in vacuo until a white solid separates upon the addition of water. The solid is collected by filtration, triturated with acetonitrile, and dried in vacuo at ambient temperature to give 1.2 g. of [[1-(amino)-3-phenylpropyl]hydroxyphosphinyl]acetic acid. Tlc, silica gel, butanol/acetic acid/water (3:1:1) shows a single ninhydrin sensitive spot, R$_f$ 0.40.

(c)
[[1-(Benzoylamino)-3-phenylpropyl]hydroxyphosphinyl]acetic acid

To a suspension of the product from part (b) (1.1 g., 0.0043 mole) in 30 ml. of water (pH 2.8), solid sodium carbonate is added until solution is effected (pH 9.0). The pH of the solution is maintained at a pH of 9-9.5 by the addition of solid sodium carbonate during the dropwise addition of a solution of benzoyl chloride (0.7 g., 0.005 mole) in 10 ml. of acetone. Tlc, silica gel, butanol/acetic acid/water (3:1:1) shows a positive ninhydrin spot at R$_f$ 0.40 plus a major PMA plus heat sensitive spot at R$_f$ 0.55. An additional equivalent of benzoyl chloride (0.7 g., 0.005 mole) in 10 ml. of acetone is added while maintaining the pH at 9-9.5 as before. Tlc shows a negative ninhydrin test. The alkaline solution is filtered (to remove solids in suspension), washed with ether and acidified to pH of 1 with concentrated hydrochloric acid. The oil that separates from solution is extracted into ethyl acetate, washed with brine, and dried (MgSO$_4$). The solvent is removed in vacuo to give 1 g. of amorphous solid [[1-(benzoylamino)-3-phenylpropyl]hydroxyphosphinyl]acetic acid. Tlc, silica gel, butanol/acetic acid/water (3:1:1) shows a single spot at $R_f$ 0.55.

(d)
(±)-1-[[[1-(Benzoylamino)-3-phenylpropyl]hydroxyphosphinyl]acetyl-4-[ethylenebis(thio)]-L-proline, methyl ester 1,1-Carbonyldiimidazole (0.5 g., 0.003 mole) is added to a cooled solution in an ice water bath of the product from part (c) (0.8 g., 0.0023 mole) in 50 ml. of tetrahydrofuran. The mixture is stirred in the cold for one hour, followed by the addition of triethylamine (0.004 mole) and 4-[ethylenebis(thio)]-L-proline, methyl ester, hydrochloric acid salt (0.8 g., 0.003 mole). The mixture is stirred at ambient temperature for 56 hours. Tlc, silica gel, butanol/acetic acid/water (3:1:1) shows a major spot at $R_f$ 0.63 plus a minor spot at $R_f$ 0.55. The solvent is removed in vacuo. The residue is dissolved in ethyl acetate (75 ml.) plus water (10 ml.). After washing with 5% potassium bisulfate to a pH of 1, followed by brine, and drying (MgSO$_4$), the solvent is removed in vacuo. The amorphous solid residue (1.1 g.) is chromatographed on silica gel, eluted with dichloromethane/methanol (95:5) followed by dichloromethane/methanol/acetic acid (95:5:5) to give 0.45 g. of amorphous solid (±)-1-[[[1-(benzoylamino)-3-phenylpropyl]hydroxyphosphinyl]acetyl]-4-[ethylenebis(thio)]-L-proline, methyl ester. Tlc shows a single spot at $R_f$ 0.66.

The 4-[ethylenebis(thio)]-L-proline, methyl ester, hydrochloric acid salt employed in the above procedure is obtained by bubbling hydrochloric acid through a solution of methanol (25 ml.) and 4-[ethylenebis(thio)-L-proline (1.3 g., 0.0053 mole) at 0° for 30 minutes. Tlc, dichloromethane/methanol/acetic (8:1:1) shows a major spot at $R_f$ 0.75. Nitrogen gas is bubbled through the solution to remove hydrochloric acid, then the methanol is stripped. Triturating the slurry several times with ether yields 1.51 g. of brown solid 4-[ethylenebis(thio)]-L-proline, methyl ester, hydrochloric acid salt.

Anal. calc'd. for $C_8H_{14}NO_2S_2Cl$: C, 37.57; H, 5.52; N, 5.48; S, 25.07; Cl, 13.86. Found: C, 36.99; H, 5.58; N, 5.40; S, 23.89; Cl, 13.93.

(e)
(±)-1-[[[1-(Benzoylamino)-3-phenylpropyl]hydroxyphosphinyl]acetyl]-4-[ethylenebis(thio)]-L-proline A solution of the product from part (d) (0.4 g., 0.007 mole) in 0.5 N sodium hydroxide (3 ml.) and methanol (5 ml.) is stirred at reflux for one hour. Tlc shows the absence of starting material. The mixture is concentrated in vacuo. After the addition of water to the residue, the turbid solution is washed with ether, filtered to remove a trace of solids, and acidified to a pH of 2 with concentrated hydrochloric acid. A white solid precipitate that separates from solution is extracted into ethyl acetate, washed with brine, and dried (MgSO$_4$). The solvent is removed in vacuo to give 0.325 g. of off-white solid (±)-1-[[[1-(benzoylamino)-3-phenylpropyl]hydroxyphosphinyl]acetyl]-4-[ethylenebis(thio)]-2-L-proline; m.p. 118°–140°; gradual decomposition.

Anal. calc'd. for $C_{25}H_{29}N_2O_6S_2P \cdot 0.75H_2O$: C, 53.41; H, 5.46; N, 4.98; S, 11.04; P, 5.51. Found: C, 53.63; H, 5.29; N, 4.58; S, 11.30; P, 5.10.

EXAMPLES 23–84

Following the procedures of Examples 20 to 22 but coupling the acylamino phosphinyl acid shown in Col. I with the imino acid ester of Col. II one obtains the product shown in Col. III. Hydrogenation of the product of Col. III, in Examples 23 to 77, yields the corresponding acid products ($R_6$ is hydrogen).

Col. I:
$$R_{19}-\overset{O}{\underset{}{C}}-NH-\overset{R_2}{\underset{}{CH}}-\overset{O}{\underset{OH}{P}}-(CH_2)_n-\overset{R_5}{\underset{}{CH}}-\overset{O}{\underset{}{C}}-OH$$

Col. II: HX

Col. III:
$$R_{19}-\overset{O}{\underset{}{C}}-NH-\overset{R_2}{\underset{}{CH}}-\overset{O}{\underset{OH}{P}}-(CH_2)_n-\overset{R_5}{\underset{}{CH}}-\overset{O}{\underset{}{C}}-X$$

| Example | $R_{19}$ | $R_2$ | n | $R_5$ | X |
|---|---|---|---|---|---|
| 23 | C$_6$H$_5$– | C$_6$H$_5$–(CH$_2$)$_2$– | one | –H | –N(L)–COOCH$_2$–C$_6$H$_5$ (prolinyl) |
| 24 | C$_6$H$_5$– | C$_6$H$_5$–(CH$_2$)$_2$– | zero | –CH$_3$ | –N(L)–COOCH$_2$–C$_6$H$_5$ with OH (4-hydroxyprolinyl) |
| 25 | C$_6$H$_5$– | C$_6$H$_5$–CH$_2$– | zero | –CH$_2$CCl$_3$ | –N(L)–COOCH$_2$–C$_6$H$_5$ with CH$_3$ (4-methylprolinyl) |

-continued

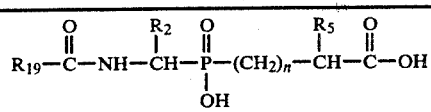 Col. I

HX Col. II

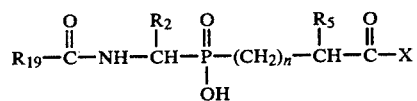 Col. III

| Example | R19 | R2 | n | R5 | X |
|---|---|---|---|---|---|
| 26 | 2-thienyl | $\phi$-CH$_2$- | zero | $\phi$-CH$_2$- | -N(L)-CH(CH$_2$C(CH$_3$)$_3$)-COOCH$_2\phi$ |
| 27 | 2-furyl | $\phi$-(CH$_2$)$_2$- | one | -H | -N(L)-CH(CH$_2$CHCl)-COOCH$_2\phi$ |
| 28 | 4-pyridyl | $\phi$-(CH$_2$)$_2$- | zero | -H | -N(L)-CH(CH$_2$C(O))-COOC(CH$_3$)$_3$ |
| 29 | $\phi$-CH$_2$- | $\phi$-(CH$_2$)$_2$- | zero | -H | -N(L)-CH(CH$_2$CHN$_3$)-COOCH$_2\phi$ |
| 30 | $\phi$-(CH$_2$)$_2$- | -H | zero | -CH$_3$ | -N(L)-CH(CH$_2$CHNHCOCH$_3$)-COOCH$_2\phi$ |
| 31 | H$_2$N-CH$_2$- | $\phi$-(CH$_2$)$_2$- | one | -H | -N(L)-CH(CH$_2$CHNHCOCH$_2\phi$)-COOCH$_2\phi$ |
| 32 | 4-F-$\phi$- | $\phi$-(CH$_2$)$_2$- | zero | -H | -N(L)-CH(CH$_2$CH$\phi$)-COOCH$_2\phi$ |
| 33 | $\phi$- | $\phi$-(CH$_2$)$_3$- | zero | -H | -N(L)-CH(CH$_2$CH$\phi$)-COOCH$_2\phi$ |
| 34 | 4-H$_3$CO-$\phi$- | $\phi$-(CH$_2$)$_2$- | zero | -H | -N(L)-CH(CH$_2$CH(CH$_2\phi$))-COOCH$_2\phi$ |

-continued
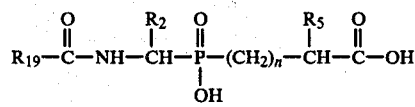 Col. I
HX Col. II
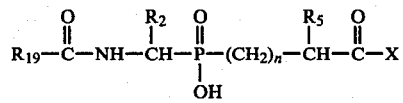 Col. III
| Example | R₁₉ | R₂ | n | R₅ | X |
|---|---|---|---|---|---|
| 35 | H | 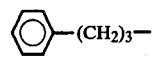 | zero | —H | 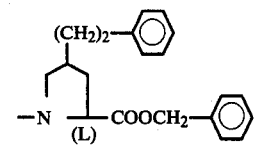 |
| 36 |  | 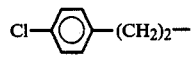 | zero | —H | 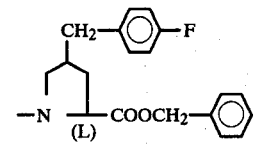 |
| 37 |  |  —CH₃ | one | —H | 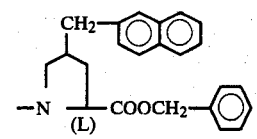 |
| 38 |  | 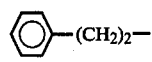 | zero | —H | 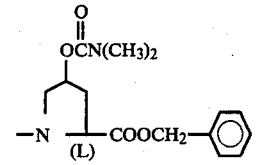 |
| 39 | 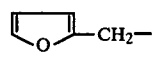 | 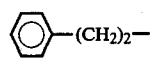 | one | —H | 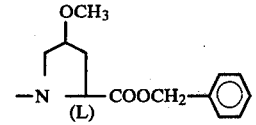 |
| 40 | 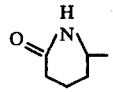 | 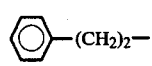 | zero | —CH₃ | 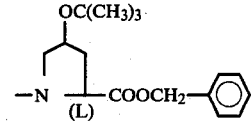 |
| 41 |  | 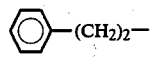 | zero | —H | 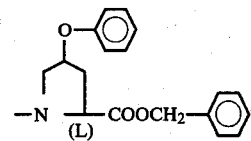 |
| 42 |  | 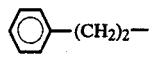 | zero | —H | 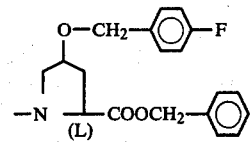 |

-continued

Col. I
$$R_{19}-\overset{O}{\overset{\|}{C}}-NH-\overset{R_2}{\overset{|}{CH}}-\overset{O}{\overset{\|}{\underset{|}{P}}}-(CH_2)_n-\overset{R_5}{\overset{|}{CH}}-\overset{O}{\overset{\|}{C}}-OH$$
$$\overset{}{\underset{OH}{}}$$

HX  Col. II

Col. III
$$R_{19}-\overset{O}{\overset{\|}{C}}-NH-\overset{R_2}{\overset{|}{CH}}-\overset{O}{\overset{\|}{\underset{|}{P}}}-(CH_2)_n-\overset{R_5}{\overset{|}{CH}}-\overset{O}{\overset{\|}{C}}-X$$
$$\overset{}{\underset{OH}{}}$$

| Example | $R_{19}$ | $R_2$ | n | $R_5$ | X |
|---|---|---|---|---|---|
| 43 | Ph— | Ph—(CH$_2$)$_2$— | zero | —H | —N(L)—CH$_2$CH(O-biphenyl)—COOCH$_2$Ph |
| 44 | Ph— | Ph—(CH$_2$)$_2$— | one | —H | —N(L)—CH$_2$CH(SCH$_3$)—COOCH$_2$Ph |
| 45 | Ph— | Ph—(CH$_2$)$_3$— | zero | —CH$_3$ | —N(L)—CH$_2$CH(SC$_2$H$_5$)—COOCH$_2$Ph |
| 46 | Ph—(CH$_2$)$_5$— | Ph—(CH$_2$)$_2$— | zero | —H | —N(L)—CH$_2$CH(S-C$_6$H$_4$-F)—COOCH$_2$Ph |
| 47 | Ph—(CH$_2$)$_4$— | Ph— | zero | —H | —N(L)—CH$_2$CH(S-CH$_2$Ph)—COOCH$_2$Ph |
| 48 | HO—C$_6$H$_4$— | Ph—(CH$_2$)$_2$— | zero | —H | —N(L)—CH$_2$CH(S-naphthyl)—COOCH$_2$Ph |
| 49 | Ph— | Ph—(CH$_2$)$_2$— | one | —CH$_3$ | —N(L)—CH$_2$CH(CH$_2$-thienyl)—COOCH$_2$Ph |
| 50 | Ph— | Ph—(CH$_2$)$_2$— | zero | —H | —N(L)—CH$_2$CH(S-C$_6$H$_4$-OCH$_3$)—COOCH$_2$Ph |
| 51 | H$_3$C— | Ph—(CH$_2$)$_2$— | zero | —H | —N(L)—CH$_2$CF$_2$—COOCH$_2$Ph |

-continued

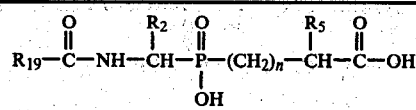 Col. I

HX Col. II

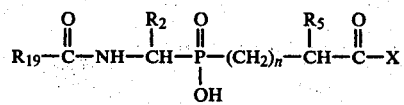 Col. III

| Example | R19 | R2 | n | R5 | X |
|---|---|---|---|---|---|
| 52 | H3C—(CH2)3— | ⟨phenyl⟩—(CH2)2— | zero | —H | 4-(dimethoxy)piperidine-2-COOCH2-phenyl (L) |
| 53 | ⟨phenyl⟩— | ⟨phenyl⟩—(CH2)2— | zero | —H | 1,3-dithiolane-spiro-piperidine-COOCH2-phenyl (L) |
| 54 | ⟨phenyl⟩— | ⟨phenyl⟩—(CH2)2— | zero | —H | 1,3-dioxolane-spiro-piperidine-COOCH2-phenyl (L) |
| 55 | ⟨phenyl⟩— | ⟨phenyl⟩—(CH2)2— | zero | —H | 1,3-dioxane-spiro-piperidine-COOCH2-phenyl (L) |
| 56 | ⟨phenyl⟩— | ⟨phenyl⟩—(CH2)3 | zero | —H | 1,3-dithiolane-spiro-piperidine-COOCH2-phenyl (L) |
| 57 | ⟨phenyl⟩— | ⟨phenyl⟩—(CH2)2 | zero | —CH3 | 4-SCH3-piperidine-COOCH2-phenyl (L) |
| 58 | ⟨phenyl⟩— | ⟨phenyl⟩—(CH2)4— | zero | —H | 4-O-phenyl-piperidine-COOCH2-phenyl (L) |
| 59 | ⟨phenyl⟩— | H3C—CH=CH— | zero | —H | 4-(O-CH2-phenyl-OCH3)-piperidine-COOCH2-phenyl (L) |
| 60 | H3C—⟨phenyl⟩— | ⟨phenyl⟩—(CH2)2— | one | —H | 4-(S-phenyl-F)-piperidine-COOCH2-phenyl (L) |

-continued

Col. I
$$R_{19}-\overset{O}{\underset{}{C}}-NH-\overset{R_2}{\underset{}{CH}}-\overset{O}{\underset{OH}{P}}-(CH_2)_n-\overset{R_5}{\underset{}{CH}}-\overset{O}{\underset{}{C}}-OH$$

Col. II
HX

Col. III
$$R_{19}-\overset{O}{\underset{}{C}}-NH-\overset{R_2}{\underset{}{CH}}-\overset{O}{\underset{OH}{P}}-(CH_2)_n-\overset{R_5}{\underset{}{CH}}-\overset{O}{\underset{}{C}}-X$$

| Example | R₁₉ | R₂ | n | R₅ | X |
|---|---|---|---|---|---|
| 61 | F₃C— | Ph–(CH₂)₂– | zero | —H | proline with –CH₂–CH₂–S–CH₂–Ph, –COOCH₂Ph (L) |
| 62 | Ph– | thienyl–(CH₂)₂– | zero | —H | dehydroproline, –COOCH₂Ph (L) |
| 63 | Ph– | furyl–(CH₂)₂– | zero | —H | proline, –COOCH₂Ph (L) |
| 64 | Ph– | pyridyl–(CH₂)₂– | zero | —H | proline, –COOCH₂Ph (L) |
| 65 | Ph– | pyridyl–(CH₂)₂– | one | —H | proline with –S–Ph, –COOCH₂Ph (L) |
| 66 | Ph– | thienyl– | zero | —CH₃ | proline with C=O, –COOCH₂Ph (L) |
| 67 | Ph– | Ph–(CH₂)₂– | zero | —H | proline with –Ph, –COOCH₂Ph (L) |
| 68 | Ph– | Ph–(CH₂)₂– | one | —H | proline with –C₆H₄–OH, –COOCH₂Ph (L) |
| 69 | Ph– | Ph–(CH₂)₂– | zero | —CH₃ | proline with C=O, –COOCH₂Ph (L) |
| 70 | Ph– | Ph–(CH₂)₂– | zero | —H | thiazolidine, –COOCH₂Ph (L) |
| 71 | Ph– | Ph–(CH₂)₂ | zero | —H | thiazolidine with (CH₃)₂C–S–C(CH₃)₂, –COOCH₂Ph (L) |

-continued

Col. I
$$R_{19}-\overset{O}{\underset{}{C}}-NH-\underset{\underset{R_2}{|}}{CH}-\underset{\underset{OH}{|}}{\overset{\overset{O}{\|}}{P}}-(CH_2)_n-\underset{\underset{R_5}{|}}{CH}-\overset{O}{\underset{}{C}}-OH$$

HX  Col. II

Col. III
$$R_{19}-\overset{O}{\underset{}{C}}-NH-\underset{\underset{R_2}{|}}{CH}-\underset{\underset{OH}{|}}{\overset{\overset{O}{\|}}{P}}-(CH_2)_n-\underset{\underset{R_5}{|}}{CH}-\overset{O}{\underset{}{C}}-X$$

| Example | $R_{19}$ | $R_2$ | $n$ | $R_5$ | X |
|---------|----------|-------|-----|-------|---|
| 72 | C₆H₅– | C₆H₅–(CH₂)₂– | zero | –H | proline-type with benzyl-S-CH₂– side chain, –COOCH₂C₆H₅ (L) |
| 73 | C₆H₅– | C₆H₅–(CH₂)₂– | zero | –H | proline-type with (4-HO-C₆H₄)-CH(S-CH₂–), –COOCH₂C₆H₅ (L) |
| 74 | C₆H₅–CH₂– | C₆H₅–(CH₂)₃– | zero | –H | pipecolic acid, –COOCH₂C₆H₅ (L) |
| 75 | C₆H₅–CH₂– | C₆H₅–(CH₂)₃– | zero | –H | proline with cyclohexyl-CH₂– side chain, –COOCH₂C₆H₅ (L) |
| 76 | C₆H₅–CH₂– | C₆H₅–(CH₂)₃– | zero | –H | proline with spiro-dithiolane, –COOCH₂C₆H₅ (L) |
| 77 | 4-F-C₆H₄– | C₆H₅–(CH₂)₂– | zero | –H | pipecolic acid, –COOCH₂C₆H₅ (L) |
| 78 | 4-H₃CO-C₆H₄–CH₂– | C₆H₅–(CH₂)₂– | zero | –H | pipecolic acid, –COOCH₂C₆H₅ (L) |
| 79 | C₆H₅– | C₆H₅–(CH₂)₂– | zero | –H | pipecolic acid, –COOCH(CH₃)OCOC(CH₃)₃ |
| 80 | C₆H₅–CH₂– | C₆H₅–(CH₂)₂– | zero | –H | pipecolic acid, –COOCH₂OCOCH₃ |
| 81 | C₆H₅– | C₆H₅–(CH₂)₃– | zero | –CH₃ | pipecolic acid, –COO– phthalide ester |

-continued $$R_{19}-\overset{O}{\overset{\|}{C}}-NH-\overset{R_2}{\overset{|}{C}H}-\overset{O}{\overset{\|}{\underset{OH}{P}}}-(CH_2)_n-\overset{R_5}{\overset{|}{C}H}-\overset{O}{\overset{\|}{C}}-OH \qquad \text{Col. I}$$

$$HX \qquad \text{Col. II}$$

$$R_{19}-\overset{O}{\overset{\|}{C}}-NH-\overset{R_2}{\overset{|}{C}H}-\overset{O}{\overset{\|}{\underset{OH}{P}}}-(CH_2)_n-\overset{R_5}{\overset{|}{C}H}-\overset{O}{\overset{\|}{C}}-X \qquad \text{Col. III}$$

| Example | $R_{19}$ | $R_2$ | n | $R_5$ | X |
|---|---|---|---|---|---|
| 83 | 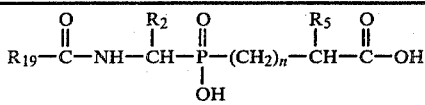 | ⬡—(CH$_2$)$_2$— | one | —H | (structure with $-N$, $S$—⬡, $COOCH_2OCOC(CH_3)_3$) |
| 84 | $H_3CO$—⬡—$CH_2$— | ⬡—(CH$_2$)$_2$— | zero | —H | (structure with $-N$, cyclohexyl, $COOCH_2OCOC_2H_5$) |

Similarly, the above compounds can be prepared by the procedure of Example 19 in which case the acylamino phosphinyl acid employed is of the formula

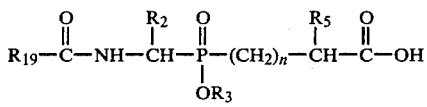

wherein $R_3$ is lower alkyl such as t-butyl, or benzyl, or benzhydryl. After the coupling reaction is completed, deprotection such as by hydrogenation yields the compounds wherein $R_3$ is hydrogen.

Also, the imino acid esters of Col. II could be employed in the procedures of Examples 1 to 18 to prepare other compounds within the scope of the invention.

Reduction of the product of Example 29 yields the corresponding 4-amino product. Similarly, the 4-keto product of Example 28 can be reacted to yield various 4-substituted amino products.

EXAMPLE 85

(±)-1-[[[1-(Benzoylamino)-3-phenylpropyl]hydroxyphosphinyl]acetyl]-L-proline (a) Methyl[3-phenyl-1-[[(phenylmethoxy)carbonyl]amino]propyl]phosphinic acid, ethyl ester Bis(trimethylsilyl)acetamide (12 g., 0.006 mole) is added via syringe, with stirring, to a solution of methyl[3-phenyl-1-[[(phenylmethoxy)carbonyl]amino]propyl]phosphinic acid (15 g., 0.047 mole), prepared for example as set forth in Example 1(a), in 75 ml. of dichloromethane. After stirring for 15 minutes the mixture is concentrated in vacuo at ambient temperature. The residue is taken up in 75 ml. of dichloromethane and then phosphorous pentachloride (11.4 g., 0.055 mole) is added portionwise, with stirring. Following the resulting vigorous, exothermic reaction, the mixture is stirred at ambient temperature for one hour. The mixture is concentrated in vacuo, the residue is dissolved in dichloromethane, cooled in an ice/water bath, and a solution of ethanol (2.8 g., 0.06 mole) and triethylamine (6 g., 0.06 mole) in dichloromethane (30 ml.) is added dropwise, with stirring, over a period of 20 minutes. The mixture is stirred at ambient temperature for 16 hours. After dilution to twice its volume with dichloromethane, the mixture is washed with water (2×50 ml.), 5% potassium bisulfate (2×35 ml.), brine, and dried (MgSO$_4$). The mixture is concentrated in vacuo to give 14.5 g. of an oil. Trituration with diisopropyl ether results in the isolation of the solid product (12 g.); m.p. 87°–95°. Tlc, silica gel, ethyl acetate shows two spots, one overlapping the other at R$_f$ 0.55 (visualized with PMA plus heat). A sample (0.5 g.) is recrystallized from diisopropyl ether (10 ml.) to give 0.39 g. of an analytical sample of methyl[3-phenyl-1-[[(phenylmethoxy)carbonyl]amino]propyl]phosphinic acid, ethyl ester; m.p. 102°–104°, sintering at 94°.

Anal. calc'd. for C$_{20}$H$_{26}$NO$_4$P: C, 63.99; H, 6.98; N, 3.73; P, 8.25. Found: C, 63.74; H, 7.10; N, 3.68; P, 8.50.

(b) [(Ethoxy)[3-phenyl-1-[[(phenylmethoxy)carbonyl]amino]propyl]phosphinyl]acetic acid A solution of 0.099 mole of lithium diisopropylamide in tetrahydrofuran (150 ml.) is prepared according to the procedure of Example 1(c) and cooled to −76°. A solution of the product from part (a) (10.3 g., 0.027 mole) in 60 ml. of tetrahydrofuran is added via syringe over a period of one hour. After stirring for 10 minutes, and warming to room temperature, the solvent is removed in vacuo. Water (50 ml.) is added to the residue and the mixture is then acidified to a pH of 1 with concentrated hydrochloric acid. The oil that separates is extracted with dichloromethane (700 ml.), washed with brine, and dried (MgSO$_4$). Tlc, silica gel, ethyl acetate, shows a major elongated spot at R$_f$ 0.15 and a minor spot at R$_f$ 0.55. The residue is dissolved in ethyl acetate (200 ml.) and extracted with saturated sodium bicarbonate solution to a pH of 10. The aqueous alkaline solution is washed with ether, acidified to a pH of 1 with concentrated hydrochloric acid, and extracted with dichloromethane (400 ml.) Tlc, silica gel, ethyl acetate, shows a single elongated spot at R$_f$ 0.15. The solution is concentrated in vacuo to give 10.3 g. of [(ethoxy)[3-phenyl-1-[[(phenylmethoxy)carbonyl]amino]propyl]phosphinyl]acetic acid as a viscous oil residue.

(c)
(±)-1-[[(Ethoxy)[3-phenyl-1-[[(phenylmethoxy)carbonyl]amino]propyl]phosphinyl]acetyl]-L-proline, 1,1-dimethylethyl ester 1,1-Carbodiimidazole (3.9 g., 0.0238 mole) is added to a chilled (0°) solution of the product from part (b) (10 g., 0.0238 mole) in acetonitrile (100 ml.). The mixture is stirred at 0° for one hour. A solution of L-proline, tert-butyl ester (4.1 g., 0.0238 mole) in acetonitrile (50 ml.) is added. After stirring at ambient temperature for 16 hours, the mixture is concentrated in vacuo. The residue is dissolved in dichloromethane (500 ml.), washed with 5% potassium bisulfate, saturated sodium bicarbonate, brine, and dried (MgSO$_4$). Tlc, silica gel, ethyl acetate, shows a major spot at R$_f$ 0.18 (visualized with PMA plus heat). The solvent is removed in vacuo. The oil residue (12 g.) is chromatographed on silica gel, eluting with ethyl acetate, acetone/ethyl acetate (1:9, 1:4) to give an oil (9.9 g.). Tlc, silica gel, acetone/ethyl acetate (1:1) shows a single spot at R$_f$ 0.44 (visualized with PMA plus heat). A portion of the residue (8.1 g.) is dissolved in diisopropyl ether (350 ml.) and allowed to stand at ambient temperature for 40 hours. A white solid (1.3 g.) is collected by filtration; m.p. 129°–135°. Tlc gives a single spot with the same R$_f$ as the mixture (R$_f$ 0.44). A portion (0.27 g.) is recrystallized from diisopropyl ether (45 ml.), with a recovery of 0.24 g. of 1-[[(ethoxy)[3-phenyl-1-[[(phenylmethoxy)carbonyl]amino]propyl]phosphinyl]acetyl]-L-proline, 1,1-dimethylethyl ester (isomer A); m.p. 135°–137°, sintering at 133°; [α]$_D$ −37° (10 mg/ml. dichloromethane).

Anal. Calc'd. for C$_{30}$H$_{41}$N$_2$O$_7$P: C, 62.92; H, 7.22; N, 4.89; P, 5.41. Found: C, 62.93; H, 7.35; N, 4.87; P, 5.40.

The filtrate is concentrated in vacuo to give 6 g. of (±)-1-[[(ethoxy)[3-phenyl-1-[[(phenylmethoxy)carbonyl]amino]propyl]phosphinyl]acetyl]L-proline, 1,1-dimethylethyl ester as an oil residue. Tlc, silica gel, acetone/ethyl acetate (1:1) shows a single spot at R$_f$ 0.45 (visualized with PMA plus heat).

(d)
(±)-1-[[[(1-(Amino)-3-phenylpropyl]ethoxyphosphinyl]acetyl]-L-proline, 1,1-dimethylethyl ester A mixture of (±)-1-[[(ethoxy)[3-phenyl-1-[[(phenylmethoxy)carbonyl]amino]propyl]phosphinyl]acetyl]-L-proline, 1,1-dimethylethyl ester from part (c) (4.5 g., 0.0085 mole) and 10% palladium on carbon catalyst (0.5 g.) in methanol/water (9:1) is stirred vigorously under one atmosphere of hydrogen until absorption ceases (overnight). Tlc, silica gel, dichloromethane/methanol/acetic acid (8:1:1) shows the absence of starting material with a major spot at R$_f$ 0.55 (ninhydrin positive, or visualized with PMA plus heat) with a minor spot at origin. The mixture is filtered and the filtrate is concentrated in vacuo to give 3.7 g. of (±)-1-[[[1-(amino)-3-phenylpropyl]ethoxyphosphinyl]acetyl]-L-proline, 1,1-dimethylethyl ester as an oil residue.

(e)
(±)-1-[[[1-(Benzoylamino)-3-phenylpropyl]ethoxyphosphinyl]acetyl]-L-proline, 1,1-dimethylethyl ester A solution of benzoic acid (1 g., 0.008 mole) and 1-hydroxybenzotriazole hydrate (1.5 g., 0.008 mole) in 30 ml. of tetrahydrofuran is cooled to 0°, followed by the portionwise addition of N,N-dicyclohexylcarbodiimide (1.7 g., 0.008 mole). The bath is removed and the mixture is stirred at ambient temperature for 70 minutes. After filtration, the filtrate is concentrated in vacuo. To the residue, dissolved in dimethylformamide (25 ml.) plus tetrahydrofuran (50 ml.), is added a solution of the product from part (d) (3.5 g., 0.008 mole) and triethylamine (0.8 g., 0.008 mole) in dimethylformamide (20 ml.). The mixture is stirred at ambient temperature for 16 hours. The solvent is then removed in vacuo. The residue is dissolved in ethyl acetate (100 ml.), washed with water, 10% citric acid, saturated sodium bicarbonate, brine, and dried (MgSO$_4$). The solvent is removed in vacuo to give an oil residue (4.2 g.). Tlc, silica gel, ethyl acetate/acetone (1:1) shows a major spot at R$_f$ 0.40 plus 3 minor spots at R$_f$ 0.64, 0.80, and 0.90. It is chromatographed on silica gel, eluted with ethyl acetate, ethyl acetate/acetone (1:1) to give 3.5 g. of (±)-1-[[[1-(benzoylamino)-3-phenylpropyl]ethoxyphosphinyl]acetyl]-L-proline, 1,1-dimethylethyl ester as an oil. Tlc shows a single spot at R$_f$ 0.33 (visualized with PMA plus heat).

(f)
(±)-1-[[[1-(Benzoylamino)-3-phenylpropyl]hydroxyphosphinyl]acetyl]-L-proline, 1,1-dimethylethyl ester Bis(trimethylsilyl)trifluoroacetamide (1.5 g., 0.006 mole) is added via syringe to a solution of the product from part (e) (3.4 g., 0.006 mole) in dichloromethane (50 ml.). The mixture is stirred for one hour and the solvent is removed in vacuo. The residue is redissolved in dichloromethane (50 ml.), and bromotrimethylsilane (1.5 g., 0.01 mole) is added via syringe. The mixture is stirred at ambient temperature for 16 hours. After concentrating in vacuo, the residue is dissolved in aqueous sodium bicarbonate (50 ml. saturated sodium bicarbonate plus 50 ml. of water). The solution is washed with ether, cooled, and acidified to a pH of 1. The oil that separates from solution is extracted into dichloromethane (200 ml.), washed with brine, and dried (MgSO$_4$). The solvent is removed in vacuo to give 2.8 g. of (±)-1-[[[(1-(benzoylamino)-3-phenylpropyl]hydroxyphosphinyl]acetyl]-L-proline, 1,1-dimethylethyl ester as an oil. Tlc, silica gel, dichloromethane/methanol/acetic acid (8:1:1) shows a single elongated spot at R$_f$ 0.66.

(g)
(±)-1-[[[1-(Benzoylamino)-3-phenylpropyl]hydroxyphosphinyl]acetyl]-L-proline A solution of the product from part (f) (2.7 g., 0.0053 mole) and anisole (6.2 g., 0.05 mole) in trifluoroacetic acid (50 ml.) is stirred at ambient temperature for one hour. The mixture is concentrated in vacuo. The residue solidifies when triturated with pentane to give 2.1 g. of product. It is then triturated with ether to give 1.9 g. of white solid (±)-1-[[[1-(benzoylamino)-3-phenylpropyl]hydroxyphosphinyl]acetyl]-L-proline; m.p. 120°–140°.

Anal. calc'd. for C$_{23}$H$_{27}$N$_2$O$_6$P.½H$_2$O: C, 59.09; H, 5.82; N, 5.99; P, 6.63. Found: C, 58.69; H, 5.64; N, 5.96; P, 6.60.

EXAMPLE 86

1-[[[1-(Benzoylamino)-3-phenylpropyl]hydroxyphosphinyl]acetyl]-L-proline 1,1-dimethylethyl ester (isomer A)

(1.4 g., 0.00265 mole), from Example 85 (c), and 10% palladium on carbon (0.1 g.) in methanol/acetic acid (9:1) is stirred vigorously under one atmosphere of hydrogen until absorption ceases. The mixture is filtered and the filtrate is concentrated in vacuo to give 1.2 g. of 1-[[[1-(amino)-3-phenylpropyl]ethoxyphosphinyl]acetyl]-L-proline, 1,1-dimethylethyl ester (isomer A) as an oil residue. Tlc, silica gel, dichloromethane/methanol/acetic acid (8:1:1) shows a major spot at $R_f$ 0.50 (ninhydrin positive, or visualized with PMA plus heat).

(b)
1-[[[1-(Benzoylamino)-3-phenylpropyl]ethoxyphosphinyl]acetyl]-L-proline, 1,1-dimethylethyl ester (isomer A)

To a solution of the product from part (a) (1.16 g., 0.0025 mole) in pyridine (15 ml.) that is cooled to 0°, is added benzoyl chloride (0.6 g., 0.004 mole). After stirring for 16 hours at ambient temperature, the mixture is concentrated in vacuo. The oil residue (1.4 g.) is chromatographed on silica gel, eluted with ethyl acetate, acetone/ethyl acetate (1:1) to give a glass-like brown solid (0.8 g.). It is dissolved in diisopropyl ether (50 ml.), treated with activated carbon, filtered, and concentrated in vacuo to give 0.66 g. of 1-[[[1-(benzoylamino)-3-phenylpropyl]ethoxyphosphinyl]acetyl]-L-proline, 1,1-dimethylethyl ester (isomer A). Tlc, silica gel, acetone/ethyl acetate (1:1) shows a single spot at $R_f$ 0.33 (visualized with PMA plus heat).

(c)
1-[[[1-(Benzoylamino)-3-phenylpropyl]hydroxyphosphinyl]acetyl]-L-proline, 1,1-dimethylethyl ester (isomer A)

Bis(trimethylsilyl)trifluoroacetamide (0.31 g., 0.0012 mole) is added via syringe to a solution of the product from part (b) (0.65 g., 0.0012 mole) in dichloromethane (10 ml.). The mixture is stirred for one hour and concentrated in vacuo. The residue is redissolved in dichloromethane (10 ml.) and bromotrimethylsilane (0.3 g., 0.002 mole) is added. The mixture is stirred at ambient temperature for 16 hours. After concentrating in vacuo, the residue is dissolved in saturated sodium bicarbonate solution (10 ml.), washed with ether, and then acidified with concentrated hydrochloric acid to a pH of 1. The oil that separates from solution is extracted into dichloromethane (50 ml.), washed with brine, and dried (MgSO4). The solvent is removed in vacuo to give 0.5 g. of 1-[[[1-(benzoylamino)-3-phenylpropyl]hydroxyphosphinyl]acetyl]-L-proline, 1,1-dimethylethyl ester (isomer A) as a glass-like solid. Tlc, silica gel, dichloromethane/methanol/acetic acid shows a major spot at $R_f$ 0.80 and a minor spot at $R_f$ 0.22 (visualized with PMA plus heat).

(d)
1-[[[1-(Benzoylamino)-3-phenylpropyl]hydroxyphosphinyl]acetyl]-L-proline (isomer A)

A solution of the product from part (c) (0.4 g., 0.008 mole) and anisole (1 ml., 0.01 mole) in trifluoroacetic acid (7 ml.) is stirred at ambient temperature for one hour. The mixture is concentrated in vacuo. The residue is triturated with pentane. The solid that separates is collected by filtration to give 0.36 g. of product; m.p. 140°–150°. It is recrystallized from acetonitrile to give 0.097 g. of 1-[[[1-(benzoylamino)-3-phenylpropyl]hydroxyphosphinyl]acetyl]-L-proline (isomer A); m.p. 157° (dec.).

Anal. calc'd. for $C_{23}H_{27}N_2O_6P \cdot 2H_2O$: C, 55.86; H, 5.50; N, 5.66; P, 6.26. Found: C, 55.74; H, 5.64; N, 5.65; P, 6.2.

EXAMPLE 87

(±)-1-[[[1-[(Cyclopentylcarbonyl)amino]-3-phenylpropyl]hydroxyphosphinyl]acetyl]-L-proline

(a)
(±)-1-[[[1-(Cyclopentylcarbonyl)amino]-3-phenylpropyl]ethoxyphosphinyl]acetyl]-L-proline, 1,1-dimethylethyl ester A solution of cyclopentanecarboxylic acid (0.26 g., 0.0023 mole) and 1-hydroxybenzotriazole hydrate (0.31 g., 0.0023 mole) in tetrahydrofuran (10 ml.) is cooled to 0°, followed by the portionwise addition of N,N-dicyclohexylcarbodiimide (0.47 g., 0.0023 mole). The bath is removed and the mixture is stirred at ambient temperature for 70 minutes. After filtration, the mixture is concentrated in vacuo. To the residue, dissolved in dimethylformamide (8 ml.) plus tetrahydrofuran (10 ml.), is added a solution of (±)-1-[[[1-(amino) 3-phenylpropyl]ethoxyphosphinyl]acetyl]-L-proline, 1,1-dimethylethyl ester (1 g., 0.0023 mole), prepared for example as described in Example 85 (d), and triethylamine (0.25 g., 0.0025 mole) in dimethylformamide (10 ml.). The mixture is stirred at ambient temperature for 16 hours. It is then concentrated in vacuo and the residue is dissolved in ethyl acetate (75 ml.), washed with water, 10% citric acid, saturated sodium bicarbonate, brine, and dried (MgSO4). The solvent is removed in vacuo to give 1.2 g. of an amber oil residue. It is chromatographed on silica gel, eluted with dichloromethane, dichloromethane/acetone (4:1) to give 1.1 g. of (±)-1-[[[1-(cyclopentylcarbonyl)amino]-3-phenylpropyl]ethoxyphosphinyl]acetyl]-L-proline, 1,1-dimethylethyl ester as an oil in two fractions: 0.8 g., Tlc, silica gel, acetone, shows a single spot at $R_f$ 0.55; and 0.3 g., Tlc, shows two spots, $R_f$ 0.55 and $R_f$ 0.52 (visualized with PMA plus heat, or $I_2$ vapor).

(b)
(±)-1-[[[1-[(Cyclopentylcarbonyl)amino]-3-phenylpropyl]hydroxyphosphinyl]acetyl]-L-proline, 1,1-dimethylethyl ester Bis(trimethylsilyl)trifluoroacetamide (0.5 g., 0.002 mole) is added to a solution of the product from part (a) (1.04 g., 0.0019 mole) in dichloromethane (20 ml.). The mixture is stirred for one hour and concentrated in vacuo. The residue is redissolved in dichloromethane (20 ml.), and bromotrimethylsilane (0.3 g., 0.002 mole) is added. The mixture is stirred at ambient temperature for 16 hours. After concentrating in vacuo, the residue is dissolved in aqueous sodium bicarbonate (15 ml. saturated sodium bicarbonate plus 10 ml. of water), washed with ether, and acidified to a pH of 1 with concentrated hydrochloric acid. The oil that separates from solution is extracted into dichloromethane, washed with brine, and dried (MgSO4). The solvent is removed in vacuo to give 0.8 g. of (±)-1-[[[1-[(cyclopentylcarbonyl)amino]-3-phenylpropyl]hydroxyphosphinyl]acetyl]-L-proline, 1,1-dimethylethyl ester as a glass-like solid. Tlc, silica gel, benzene/acetic acid (7:3) shows a single spot at R$_f$ 0.33 (visualized with PMA plus heat, or I$_2$ vapor).

(c)
(±)-1-[[[1-[(Cyclopentylcarbonyl)amino]-3-phenyl-propyl]hydroxyphosphinyl]acetyl]-L-proline A solution of the product from part (b) (0.8 g., 0.0016 mole) and anisole (1.5 ml., 0.013 mole) in trifluoroacetic acid (15 ml.) is stirred at ambient temperature for 2 hours. The mixture is concentrated in vacuo. The residue solidifies after trituration with pentane, followed by trituration with diisopropyl ether, to give 0.72 g. of material. It is dissolved in sodium bicarbonate solution (20 ml. of water plus saturated sodium bicarbonate to a pH of 8-9), washed with ether, and acidified to a pH of 1 with concentrated hydrochloric acid. The oil that separates from solution is extracted into dichloromethane, washed with brine, and dried (MgSO$_4$). The solution is concentrated in vacuo to give 0.35 g. of (±)-1-[[[1-[(cyclopentylcarbonyl)amino]-3-phenylpropyl]hydroxyphosphinyl]acetyl]-L-proline. Tlc, silica gel, butanol/acetic acid/water (3:1:1) shows a single spot at R$_f$ 0.52 (visualized with PMA plus heat, or with I$_2$ vapor).

Anal. calc'd. for $C_{22}H_{31}N_2O_6P \cdot H_2O$: C, 56.40; H, 6.67; N, 5.98; P, 6.61. Found: C, 56.43; H, 6.55; N, 6.01; P, 6.40.

EXAMPLE 88

(±)-1-[[Hydroxy[1-(1-oxohexyl)amino]-3-phenyl-propyl]phosphinyl]acetyl]-L-proline (a)
(±)-1-[[Ethoxy[1-[(1-oxohexyl)amino]-3-phenyl-propyl]phosphinyl]acetyl]-L-proline, 1,1-dimethylethyl ester To a solution of (±)-1-[[[1-(amino)-3-phenylpropyl]ethoxyphosphinyl]acetyl]-L-proline, 1,1-dimethylethyl ester (1.2 g., 0.0027 mole), prepared for example as described in Example 85 (d), and triethylamine (0.28 g., 0.0027 mole) in dichloromethane (20 ml.), 1-hydroxybenzotriazole hydrate (0.36 g., 0.0027 mole) is added. The mixture is cooled to 0°, followed by dropwise addition of a solution of hexanoyl chloride (0.36 g., 0.0027 mole) in dichloromethane (10 ml.). After stirring for 16 hours, the mixture is concentrated in vacuo. The residue is dissolved in ethyl acetate, washed with water, 10% citric acid, saturated sodium bicarbonate, brine, and dried (MgSO$_4$). The solvent is removed in vacuo to give an oil residue of 1.7 g. It is chromatographed on silica gel, eluted with dichloromethane followed by dichloromethane/acetone (4:1) to give 0.78 g. of (±)-1-[[ethoxy[1-[(1-oxohexyl)amino]-3-phenylpropyl]phosphinyl]acetyl]-L-proline, 1,1-dimethylethyl ester. Tlc, silica gel, acetone, shows a single spot at R$_f$ 0.60 (visualized with PMA plus heat).

(b)
(±)-1-[[Hydroxy[1-[(1-oxohexyl)amino]-3-phenyl-propyl]phosphinyl]acetyl]-L-proline, 1,1-dimethylethyl ester Bis(trimethylsilyl)trifluoroacetamide (0.36 g., 0.0014 mole) is added to a solution of the product from part (a) (0.73 g., 0.00136 mole) in dichloromethane (20 ml.). The mixture is stirred for one hour and concentrated, at ambient temperature, in vacuo. The residue is redissolved in dichloromethane (20 ml.), and bromotrimethylsilane (0.25 g., 0.0014 mole) is added. After stirring at ambient temperature for 16 hours, the mixture is concentrated in vacuo and the residue is dissolved in aqueous sodium bicarbonate (10 ml. of water plus 15 ml. of saturated sodium bicarbonate). The turbid solution is washed with ether and acidified to a pH of 1 with concentrated hydrochloric acid. The oil that separates from solution is extracted into dichloromethane, washed with brine, and dried (MgSO$_4$). The solvent is removed in vacuo to give 0.6 g. of (±)-1-[[hydroxy[1-[(1-oxohexyl)amino]-3-phenylpropyl]phosphinyl]acetyl]-L-proline, 1,1-dimethylethyl ester as a colorless oil. Tlc, silica gel, benzene/acetic acid (7:3) shows a single spot at R$_f$ 0.38 (visualized with PMA plus heat, or I$_2$ vapor).

(c)
(±)-1-[[Hydroxy[1-[(1-oxohexyl)amino]-3-phenyl-propyl]phosphinyl]acetyl]-L-proline A solution of the product from part (b) (0.57 g., 0.0011 mole) and anisole (2 g., 0.018 mole) in trifluoroacetic acid (15 ml.) is stirred at ambient temperature for 2 hours. The mixture is concentrated in vacuo. The residue solidifies after trituration with pentane, followed by trituration with diisopropyl ether, to give 0.46 g. of material. It is dissolved in sodium bicarbonate solution (15 ml. of water plus saturated sodium bicarbonate to a pH of 8-9), washed with ether, and acidified to a pH of 1 with concentrated hydrochloric acid. The oil that separates from solution is extracted into dichloromethane, washed with brine, and dried (MgSO$_4$). The solution is concentrated in vacuo to give 0.37 g. of (±)-1-[[hydroxy[1-[(1-oxohexyl)amino]-3-phenylpropyl]phosphinyl]acetyl]-L-proline as an amorphous solid. Tlc, silica gel, butanol/acetic acid/water (3:1:1) shows a single spot at R$_f$ 0.50 (visualized with PMA plus heat, or with I$_2$ vapor).

Anal. Calc'd. for $C_{22}H_{33}N_2O_6P \cdot H_2O$: C, 56.16; H, 7.00; N, 5.88; P, 6.58. Found: C, 55.92; H, 7.35; N, 5.95; P, 6.40.

EXAMPLE 89

(±)-1-[[Hydroxy[1-[[(5-oxo-2-pyrrolidinyl)carbonyl]amino]-3-phenylpropyl]phosphinyl]acetyl]-L-proline (a) (±)-1-[[Ethoxy[1-[[(B 5-oxo-2-pyrrolidinyl)carbonyl]amino]-3-phenylpropyl]-phosphinyl]acetyl]-L-proline, 1,1-dimethylethyl ester A solution of L-2-pyrrolidone-5-carboxylic acid (0.3 g., 0.0023 mole) and 1-hydroxybenzotriazole hydrate (0.31 g., 0.0023 mole) in tetrahydrofuran (10 ml.) is chilled to 0° and 1,1-dicyclohexylcarbodiimide (0.47 g., 0.0023 mole) is added. The cooling bath is removed and the mixture is stirred at ambient temperature for 70 minutes. The solids separating from solution are in excess of an equivalent of dicyclohexylurea. Dimethylformamide (15 ml.) and tetrahydrofuran (10 ml.) are added, followed by a solution of (±)-1-[[[1-(amino)-3-phenylpropyl]ethoxyphosphinyl]acetyl]-L-proline, 1,1-dimethylethyl ester (0.1 g., 0.0023 mole), prepared for example according to the procedure of Example 85 (d), and triethylamine (0.25 g., 0.0024 mole) in dimethylformamide (10 ml.). The mixture is stirred at ambient temperature for 16 hours. After filtration, the filtrate is concentrated in vacuo. The residue is dissolved in ethyl acetate (75 ml.), washed with water, 10% citric acid, sodium bicarbonate, brine, and dried (MgSO$_4$). The solvent is removed in vacuo to give 1.1 g. of a glass-like solid residue. Chromatography on silica gel, eluting with dichloromethane, dichloromethane/acetone (4:1), acetone gives 0.58 g. of (±)-1-[[ethoxy[1-[[(5-oxo-2- pyrrolidinyl)carbonyl]amino]-3-phenylpropyl]phosphinyl]acetyl]-L-proline, 1,1-dimethylethyl ester. Tlc, silica gel, acetone shows a single spot at $R_f$ 0.20 (visualized with PMA plus heat, or $I_2$ vapor).

(b)
(±)-1-[[Hydroxy[1-[[(5-oxo-2-pyrrolidinyl)carbonyl]amino]-3-phenylpropyl]phosphinyl]acetyl]-L-proline, 1,1-dimethyl ester A solution of the product from part (a) (0.54 g., 0.001 mole) in dichloromethane (10 ml.) is treated with bromotrimethylsilane (0.3 g., 0.002 mole). The mixture is stirred at ambient temperature for 16 hours. After concentrating in vacuo, the residue is treated with water (5 ml.) and extracted into dichloromethane (75 ml.). It is washed with brine, dried (MgSO4), and the solvent is removed in vacuo to give 0.38 g. of (±)-1-[[hydroxy[1-[[(5-oxo-2-pyrrolidinyl) carbonyl]amino]-3-phenylpropyl]phosphinyl]acetyl]-L-proline, 1,1-dimethylethyl ester as a glasslike solid. Tlc, silica gel, butanol/acetic acid/water (3:1:1) shows a single spot at $R_f$ 0.53 (visualized with PMA plus heat or with $I_2$ vapor).

(c)
(±)-1-[[Hydroxy[1-[[(5-oxo-2-pyrrolidinyl)carbonyl]amino]-3-phenylpropyl]phosphinyl]acetyl]-L-proline A solution of the product from part (b) (0.37 g., 0.0007 mole) and anisole (1 g., 0.01 mole) in trifluoroacetic acid (7 ml.) is stirred at ambient temperature for 2 hours. After concentrating in vacuo, the residue solidifies when triturated with pentane and with diisopropyl ether, to give 0.38 g. of material. It is dissolved in water (40 ml.), washed with ether, millipore filtered, and lyophilized to give 0.28 g. of (±)-1-[[hydroxy[1-[[(5-oxo-2-pyrrolidinyl) carbonyl]amino]-3-phenylpropyl]phosphinyl]acetyl]-L-proline. Tlc, silica gel, butanol/acetic acid/water (3:1:1) shows a single spot at $R_f$ 0.28 (visualized with PMA plus heat, or with $I_2$ vapor).

Anal. calc'd. for $C_{21}H_{28}N_3O_7P\cdot 2.5 H_2O$: C, 49.50; H, 5.52; N, 8.23; P, 6.06. Found: C, 49.60; H, 5.66; N, 8.11; P, 5.80.

EXAMPLE 90

[1(±),4S]-1-[[[1-(Benzoylamino)-3-phenylpropyl]hydroxyphosphinyl]acetyl]-4-(phenylmethyl)-L-proline (a)
[1(±),4S]-1-[[Ethoxy[3-phenyl-1-[[(phenylmethoxy)carbonyl]amino]propyl]phosphinyl]acetyl]4-(phenylmethyl)-L-proline 1,1-Carbonyldiimidazole (0.4 g., 0.00238 mole) is added to a cooled solution (ice/water bath) of (±)-[(ethoxy)[3-phenyl-1-[[(phenylmethoxy)carbonyl]amino]propyl]phosphinyl]acetic acid (1 g., 0.00238 mole), prepared for example according to the procedure of Example 85 (b), in acetonitrile (10 ml.). The mixture is stirred in the cold for one hour and a suspension of (4S)-4-(phenylmethyl)-L-proline (0.49 g., 0.00238 mole, as its triethylammonium salt) in acetonitrile (10 ml.) is added to the cold solution. The mixture is stirred at ambient temperature for 16 hours and concentrated in vacuo. The residue is dissolved in dichloromethane (100 ml.), washed with 5% potassium bisulfate to a pH of 4, washed with brine, dried (MgSO4), and concentrated in vacuo. The residue (1.4 g.) is chromatographed on silica gel, eluting with acetic acid/benzene (1:9, 3:17, 1:4) to give 1.1 g. of [1(±),4S]-1-[[ethoxy[3-phenyl-1-[[(phenylmethoxy)carbonyl]amino]propyl]phosphinyl]acetyl]-4-(phenylmethyl)-L-proline as a viscous oil. Tlc, silica gel, benzene/acetic acid (4:1) shows a single elongated spot at $R_f$ 0.22 (visualized with PMA plus heat).

The cis-4-(phenylmethyl)-L-proline employed above can be prepared as described by Krapcho in U.S. Ser. No. 164,985, now U.S. Pat. No. 4,316,905, i.e.:

To a 1 liter flask are added 7.6 g. (0.16 mole) of sodium hydride (50% suspension) and 150 ml. of dry dimethylsulfoxide. The suspension is stirred and then maintained at 70° for thirty minutes (all of the sodium hydride has reacted at this point). The solution is cooled to 30° and treated portionwise with a suspension of 61.1 g. (0.16 mole) of benzyltriphenyl phosphonium chloride (dried in vacuo overnight) in 150 ml. dimethylsulfoxide and the resulting intense red suspension is heated to 70°. This mixture is cooled to 25° and treated with a solution of 13.2 g. (0.05 mole) of N-carbobenzyloxy-4-keto-L-proline in 40 ml. of dimethylsulfoxide over a period of twenty minutes. This mixture is maintained at 65°–70° for four hours, allowed to stand overnight at room temperature, and then poured onto a solution of 10 g. of potassium bicarbonate in 400 ml. of ice-water. Some ice is added to the mixture to bring the volume to 1 liter and it is then extracted three times with 250 ml. portions of ether. The ether phases are discarded and the aqueous phase is cooled and acidified with 50 ml. of 6 N hydrochloric acid. The product is extracted with 250 ml. of chloroform and then twice with 100 ml. of chloroform. The organic phases are combined, dried (MgSO4), filtered and the solvent evaporated to give 10.2 g. of pale brown viscous residue. The latter is triturated with 500 ml. of ether. The ether is decanted from the brown residue (mostly triphenylphosphineoxide) and the latter is triturated twice with 100 ml. of ether. The ether phases are combined, cooled and treated portionwise with a solution of 10 g. of sodium bicarbonate in 200 ml. of water. The layers are separated and the organic phase is extracted with 10 ml. of water. The ether phase is discarded and the aqueous phases are combined, cooled, acidified with 18 ml. of 6 N hydrochloric acid and extracted three times with 100 ml. of ether. The organic layers are combined, dried (MgSO4), filtered and the solvent evaporated to give 8.9 g. (52.6%) of a pale yellow foam. The bulk of this compound (8.6 g.) is dissolved in 20 ml. of acetonitrile and treated with 4.6 g. of dicyclohexylamine. The product slowly crystallizes. After standing overnight in the cold, the nearly colorless dicyclohexylamine salt is filtered and dried to yield 11.0 g. of N-carbobenzyloxy-4-(phenylmethylene)-L-proline, dicyclohexylamine; m.p. 142°–150°. After recrystallization from 65 ml. of acetonitrile, 9.5 g. of nearly colorless dicyclohexylamine salt are obtained; m.p. 150°–155°; $[\alpha]_D^{25}$ +7.7° (c, 1% in chloroform).

Anal. Calc'd. for $C_{20}H_{19}NO_4\cdot C_{12}H_{23}N$: C, 74.09; H, 8.16; N, 5.40. Found: C, 73.87; H, 8.18; N, 5.33.

This dicyclohexylamine salt (9.4 g.) is suspended in 100 ml. of ethyl acetate and treated with 100 ml. of 10% potassium bisulfate. The mixture is shaken and the aqueous phase is extracted twice with 50 ml. of ethyl acetate. The organic phases are combined, dried, (MgSO4), filtered and the solvent evaporated to give 6.4 g. (38%) of pale yellow foam-like solid N-carbobenzyloxy-4-(phenylmethylene)-L-proline; $[\alpha]_D^{25}$ −2.5° (c, 1% in chloroform); $R_f$ 0.29 (85:15 toluene:acetic acid on silica gel).

A solution of 6.1 g. of N-carbobenzyloxy-4-(phenylmethylene)-L-proline in 200 ml. of ethyl acetate is treated with 0.6 g. of platinum dioxide. The mixture is shaken under one atmosphere of hydrogen. Initially the uptake of hydrogen is rapid and essentially ceases in thirty minutes. The colorless solution is filtered and the filtrate is concentrated to give 5.7 g. of N-carbobenzyloxy-cis-4-(phenylmethyl)-L-proline. The latter is dissolved in 200 ml. of methanol and 30 ml. of water and treated with a slurry of 2 g. of 5% palladium-carbon catalyst in 70 ml. of methanol. The mixture is shaken under two atmospheres of hydrogen. The uptake of hydrogen is essentially complete in forty minutes. After seventy minutes, the catalyst is filtered through a celite bed and the filtrate concentrated to give 3.3 g. (89%) of pale gray solid cis-4-(phenylmethyl)-L-proline; m.p. 200°–201° (dec.); $[\alpha]_D^{25}$ –3.5° (c, 1% in N-hydrochloric acid). A small amount of catalyst is present in this material.

Anal. Calc'd. for $C_{12}H_{15}NO_2 \cdot \frac{1}{4}H_2O$: C, 68.71; H, 7.45; N, 6.68. Found: C, 68.21; H, 7.62; N, 6.56.

A solution of the hydrochloride salt of cis-4-(phenylmethyl)-L-proline (0.58 g., 0.0024 mole) in methanol (10 ml.) is treated with two equivalents of triethylamine (0.5 g., 0.0048 mole) in methanol (5 ml.). The mixture is stirred at ambient temperature for 5 minutes and concentrated in vacuo. A suspension of the resulting solid in acetonitrile (10 ml.) is utilized in the reaction described above.

(b)
[1(±),4S]-1-[[[1-(Amino)-3-phenylpropyl]-ethoxyphosphinyl]acetyl]-4-(phenylmethyl)-L-proline A mixture of [1(±),4S]-1-[[ethoxy[3-phenyl-1-[[(phenylmethoxy)carbonyl]amino]propyl]phosphinyl]acetyl]-4-(phenylmethyl)-L-proline (0.9 g., 0.00148 mole), from part (a), and 10% palladium on carbon catalyst (80 mg.) in methanol/water (9:1) is stirred vigorously in an atmosphere of hydrogen until hydrogen is no longer consumed (overnight). The mixture is filtered and concentrated in vacuo to give 0.7 g. of [1(±),4S]-1-[[[1-(amino)-3-phenylpropyl]ethoxyphosphinyl]acetyl]-4-(phenylmethyl)-L-proline as a glass-like solid. Tlc, silica gel, dichloromethane/methanol/acetic acic (8:1:1) shows a single elongated spot at $R_f$ 0.30 (visualized with ninhydrin indicator plus heat, and/or PMA plus heat).

(c)
[1(±),4S]-1-[[[1-(Benzoylamino)-3-phenylpropyl]ethoxyphosphinyl]acetyl]-4-(phenylmethyl)-L-proline A solution of benzoic acid (0.185 g., 0.00148 mole) and 1-hydroxybenzotriazole hydrate (0.2 g., 0.00148 mole) in tetrahydrofuran (10 ml.) is cooled to 0°, followed by the portionwise addition of N,N-dicyclohexylcarbodiimide (0.3 g., 0.00148 mole). The bath is removed and the mixture is stirred at ambient temperature for 70 minutes. After the addition of dimethylformamide (5 ml.) to the resulting slurry, a solution of the product from part (b) (0.7 g., 0.00148 mole) and triethylamine (0.3 g., 0.003 mole) in dimethylformamide (4 ml.) is added and the mixture is stirred at ambient temperature for 16 hours. The solids are removed by filtration, washed with ethyl acetate, and the filtrate is concentrated in vacuo. The residue is dissolved in ethyl acetate (50 ml.). After filtration, the solution is washed with water (2×5 ml.), 10% citric acid (2×5 ml.), brine, and dried (MgSO$_4$). It is concentrated in vacuo to give 0.95 g. of an amber glass-like solid. Tlc, silica gel, dichloromethane/water/acetic acid (8:1:1) shows a major spot at $R_f$ 0.50. It is chromatographed on silica gel, eluting with benzene/acetic acid (4:1, 7:3) to give 0.6 g. of the product as an orange solid. Tlc, silica gel, benzene/acetic acid (7:3) shows two spots, $R_f$ 0.40 and 0.46 with a minor spot at $R_f$ 0.65. The solid is treated with one equivalent of sodium hydroxide, diluted to a volume of 10 ml. with water resulting in the separation of a solid. The alkaline mixture is acidified to a pH of 1 with concentrated hydrochloric acid. The solid that separates from solution is extracted into dichloromethane (50 ml.), washed with brine, and dried (MgSO$_4$). The mixture is concentrated in vacuo to give 0.4 g. of [1(±),4S]-1-[[[1-(benzoylamino)-3-phenylpropyl]ethoxyphosphinyl]acetyl]-4-(phenylmethyl)-L-proline as an orange solid. Tlc, silica gel, dichloromethane/methanol/acetic acid (8:1:1) shows a single spot at $R_f$ 0.80 (visualized with PMA plus heat).

(d)
[1(±),4S]-1-[[[1-(Benzoylamino)-3-phenylpropyl]hydroxyphosphinyl]acetyl]-4-(phenylmethyl)-L-proline A solution of the product from part (c) (0.37 g., 0.00064 mole) and bis(trimethylsilyl)trifluoroacetamide (0.33 g., 0.00128 mole) in dichloromethane (6 ml.) is stirred at ambient temperature for one hour. The mixture is concentrated in vacuo. The residue is dissolved in dichloromethane (8 ml.) and bromotrimethylsilane (0.2 g., 0.00128 mole) is added. The mixture is stirred at ambient temperature for 16 hours. After concentrating in vacuo, the residue is dissolved in aqueous sodium bicarbonate (3 ml. of saturated sodium bicarbonate plus 22 ml. of water), washed with ether, followed by dichloromethane, cooled, and acidified to a pH of 1 with concentrated hydrochloric acid. The amber oil that separates from solution is extracted into dichloromethane, washed with brine, and dried (MgSO$_4$). The solvent is removed in vacuo to give 0.33 g. of [1(±),4S]-1-[[[1-(benzoylamino)-3-phenylpropyl]hydroxyphosphinyl]acetyl]-4-(phenylmethyl)-L-proline as an amorphous solid; m.p. 127°–157°. Tlc, silica gel, butanol/acetic acid/water (3:1:1), shows a single spot at $R_f$ 0.60 (visualized with PMA plus heat, or with I$_2$ vapor).

Anal. calc'd. for $C_{30}H_{33}N_2O_6P \cdot 1H_2O$: C, 63.59; H, 5.87; N, 4.94; P, 5.46. Found: C, 63.40; H, 5.64; N, 4.64; P, 5.64.

In an analogous manner, the procedure of Examples 84 and 86 to 89 could be employed to prepare the compounds of Examples 18 to 83.

EXAMPLE 91

(±)-1-[[[1-(Benzoylamino)-3-phenylpropyl]hydroxyphosphinyl]acetyl]-L-proline, (2,2-dimethyl-1-oxoproxy)methyl ester, lithium salt (a)
(±)-1-[[[1-(Benzoylamino)-3-phenylpropyl]hydroxyphosphinyl]acetyl]-L-proline, (2,2-dimethyl-1-oxopropoxy)methyl ester Chloromethyl pivalate (0.23 g., 0.0015 mole) is added to a solution of (±)-1-[[[1-(benzoylamino)-3-phenylpropyl]hydroxyphosphinyl]acetyl]-L-proline (0.6 g., 0.0013 mole), prepared for example as set forth in Example 85, and triethylamine (0.2 g., 0.002 mole) in dimethylformamide (5 ml.). The mixture is stirred at ambient temperature. An additional quantity of triethylamine (0.2 g., 0.002 mole) is added after four hours. After 16 hours, Tlc shows that the reaction is incomplete. Additional triethylamine (0.2 g., 0.002 mole) and chloromethyl pivalate (0.23 g., 0.0015 mole) are added, and the mixture is stirred at ambient temperature for an additional 24 hours (Tlc shows the absence of starting material). After the addition of water (20 ml.), 10% citric acid is added immediately to a pH of 3-4. The mixture is extracted with ethyl acetate, washed with water, brine, and dried (MgSO$_4$). After concentration in vacuo, the residue of 0.8 g. of amber oil is chromatographed on silica gel, eluting with dichloromethane/methanol/acetic acid (25:1:1) to give 0.4 g. of (±)-1-[[[1-(benzoylamino)-3-phenylpropyl]hydroxyphosphinyl]acetyl]-L-proline, (2,2-dimethyl-1-oxopropoxy)-methyl ester as a glass-like solid. Tlc, silica gel, butanol-/acetic acid/water (3:1:1) shows a single spot at R$_f$0.64.

(b)
(±)-1-[[[1-(Benzoylamino)-3-phenylpropyl]hydroxy-phosphinyl]acetyl]-L-proline, (2,2-dimethyl-1-oxopropoxy)methyl ester, lithium salt To a solution of the ester product from part (a) (0.286 g., 0.005 mole) in acetone (10 ml.), a 0.25 M solution of lithium carbonate (10 ml.) is added dropwise, with stirring. As the solution becomes turbid during the addition, the turbidity is clarified by the addition of acetone, so that the final volume of the mixture is 30 ml. After filtration, to remove a trace of solids, the solution is concentrated in vacuo to a volume of 15 ml., and water is added to incipient turbidity. The mixture is millipore filtered and lyophilized to give 0.2 g. of pink colored solid. Tlc, silica gel, butanol/acetic acid/water (3:1:1) shows a single spot at R$_f$0.62 and a shadow at R$_f$0.44. The solid is placed on a column of HP-20 AG (10 ml.) and eluted with water; water/acetone in a gradient of 1-100% acetone (1;1;4;10;50;100%) to give 46 mg. of (±)-1-[[[1-(benzoylamino)-3-phenylpropyl]hydroxy-phosphinyl]acetyl]-L-proline, (2,2-dimethyl-1-oxopropoxy)methyl ester, lithium salt. Tlc, silica gel, butanol/acetic acid/water (3:1:1) shows a single spot at R$_f$ 0.62.

Anal. Calc'd. for $C_{29}H_{36}N_2O_8P\cdot Li\cdot 2.5H_2O$: C, 55.84; H, 6.62; N, 4.49; P, 4.96. Found: C, 56.04; H, 6.44; N, 4.19; P, 4.60.

EXAMPLE 92

(±)-1-[[[1-(Benzoylamino)-4-phenylbutyl][(2,2-dimethyl-1-oxopropoxy)methoxy]phosphinyl]acetyl]-L-proline (a)
(±)-1-[[[1-(Benzoylamino)-4-phenylbutyl][(2,2-dimethyl-1-oxopropoxy)methoxy]phosphinyl]acetyl]-L-proline, phenylmethyl ester A equimolar mixture of triethylamine and chloromethyl pivalate are added to a solution of (±)-1-[[[1-(benzoylamino)-4-phenylbutyl]hydroxyphosphinyl]acetyl]-L-proline, phenylmethyl ester, prepared for example as set forth in Example 20 (d), in dimethylformamide under an argon atmosphere. The mixture is stirred for several hours at room temperature, diluted with ethyl acetate, washed with water, brine, dried (MgSO$_4$), and evaporated. The crude product is chromatographed to give (±)-1-[[[1-(benzoylamino)-4-phenylbutyl][(2,2-dimethyl-1-oxopropoxy)methoxy]phosphinyl]acetyl]-L-proline, phenylmethyl ester.

(b)
(±)-1-[[[1-(Benzoylamino)-4-phenylbutyl][(2,2-dimethyl-1-oxopropoxy)methoxy]phosphinyl]acetyl]-L-proline A solution of the diester product from part (a) in methanol is added to a 10% palladium on carbon catalyst and the resulting mixture is shaken in a Parr hydrogenation apparatus for several hours. The catalyst is filtered off and the methanol is stripped from the filtrate. The crude product is chromatographed on silica gel to yield (±)-1-[[[1-(benzoylamino)-4-phenylbutyl][(2,2-dimethyl-1-oxopropoxy)methoxy]phosphinyl]acetyl]-L-proline.

EXAMPLES 93-97

Following the procedure of Example 92 but employing the alkylating agent shown in Col. I for the chloromethyl pivalate, one obtains the product listed in Col. II.

| Example | Col. I | Col. II |
|---|---|---|
| 93 | Br—CH$_2$—O—C(=O)—CH$_3$ | (±)-1-[[[1-benzoylamino)-4-phenyl-butyl][(acetyloxy)methoxy]phosphinyl]-acetyl]-L-proline |
| 94 | Cl—CH$_2$—O—C(=O)—OC$_2$H$_5$ | (±)-1-[[[1-(benzoylamino)-4-phenylbutyl][(ethoxycarbonyloxy)methoxy]phosphinyl]acetyl]-L-proline |
| 95 | 3-bromo-1(3H)-isobenzofuranone (Br on CH adjacent to C=O of phthalide) | (±)-1-[[[1-(benzoylamino)-4-phenylbutyl](1,3-dihydro-3-oxo-1-isobenzofuranyloxy)-phosphinyl]acetyl]-L-proline |
| 96 | ClCH$_2$O—C(=O)—C$_6$H$_5$ | (±)-1-[[[1-(benzoylamino)-4-phenylbutyl][(benzoyloxy)methoxy]phosphinyl]acetyl]-L-proline |
| 97 | Cl—CH(CH$_3$)—O—C(=O)—CH$_3$ | (±)-1-[[[1-(benzoylamino)-4-phenylbutyl][1-(acetyloxy)ethoxy]phosphinyl]acetyl]-L-proline |

Similarly, the alkylating agents of Examples 92 to 97 can be employed with ester products of Examples 23 to 84 to yield other compounds within the scope of this invention.

EXAMPLE 98

1000 tablets each containing the following ingredients:

| | |
|---|---|
| (±)-1-[[[1-(Benzoylamino)-3-phenylpropyl]hydroxyphosphinyl]acetyl]-L-proline | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the (±)-1-[[[1-(benzoylamino)-3-phenylpropyl]hydroxyphosphinyl]acetyl]-L-proline and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 84 and 86 to 97 can be prepared.

EXAMPLE 99

1000 tablets each containing the following ingredients:

| | |
|---|---|
| (±)-1-[[[1-(Benzoylamino)-3-phenylpropyl]hydroxyphosphinyl]acetyl]-4-[ethylenebis(thio)]-L-proline | 50 mg. |
| Lactose | 25 mg. |
| Avicel | 38 mg. |
| Corn starch | 15 mg. |
| Magnesium stearate | 2 mg. |
| | 130 mg. | are prepared from sufficient bulk quantities by mixing the (±)-1-[[[1-(benzoylamino)-3-phenylpropyl]hydroxyphosphinyl]acetyl]-4-[ethylenebis(thio)]-L-proline, lactose, and Avicel and then blending with the corn starch. Magnesium stearate is added and the dry mixture is compressed in a tablet press to form 1000 tablets each containing 50 mg. of active ingredient. The tablets are coated with a solution of Methocel E 15 (methyl cellulose) including as a color a lake containing yellow #6.

In a similar manner, tablets containing 50 mg. of the product of any of Examples 1 to 21 and 23 to 97 can be prepared.

EXAMPLE 100

Two piece #1 gelatin capsules each containing 100 mg. of (±)-1-[[[1-(benzoylamino)-4-phenylbutyl]hydroxyphosphinyl]acetyl]-L-proline are filled with a mixture of the following ingredients:

| | |
|---|---|
| (±)-1-[[[1-(benzoylamino)-4-phenylbutyl]hydroxyphosphinyl]acetyl]-L-proline | 100 mg. |
| Magnesium stearate | 7 mg. |
| Lactose | 193 mg. |

In a similar manner, capsules containing 100 mg. of the product of any of Examples 1 to 19 and 21 to 96 can be prepared.

EXAMPLE 101

An injectable solution is prepared as follows:

| | |
|---|---|
| (±)-1-[[[1-[(Ethoxycarbonyl)amino]-3-phenylpropyl]hydroxyphosphinyl]acetyl]-L-proline | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 17 and 19 to 97.

EXAMPLE 102

1000 tablets each containing the following ingredients:

| | |
|---|---|
| (±)-1-[[[1-(Benzoylamino)-3-phenylpropyl]hydroxyphosphinyl]acetyl]-L-proline | 100 mg. |
| Avicel | 100 mg. |
| Hydrochlorothiazide | 12.5 mg. |
| Lactose | 113 mg. |
| Corn starch | 17.5 mg. |
| Stearic acid | 7 |
| | 350 mg. | are prepared from sufficient bulk quantities by slugging the (±)-1-[[[1-(benzoylamino)-3-phenylpropyl]hydroxyphosphinyl]acetyl]-L-proline, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 84 and 85 to 97.

What is claimed is:

1. A compound of the formula $$R_1-HN-\underset{\underset{R_2}{|}}{CH}-\underset{\underset{OR_3}{|}}{\overset{\overset{O}{\|}}{P}}-(CH_2)_n-\underset{\underset{R_5}{|}}{CH}-\overset{\overset{O}{\|}}{C}-X$$

wherein
X is an imino acid of the formula

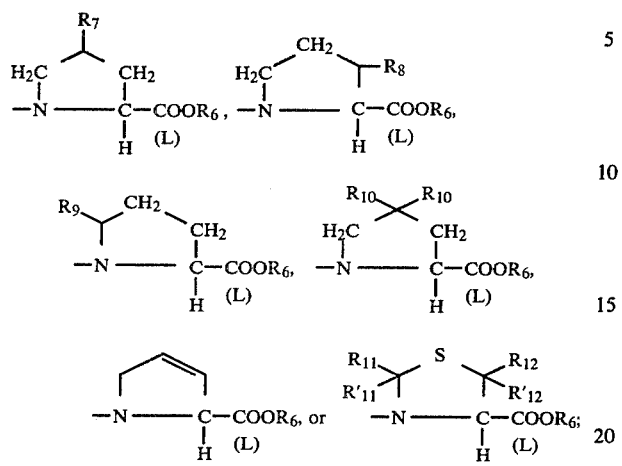

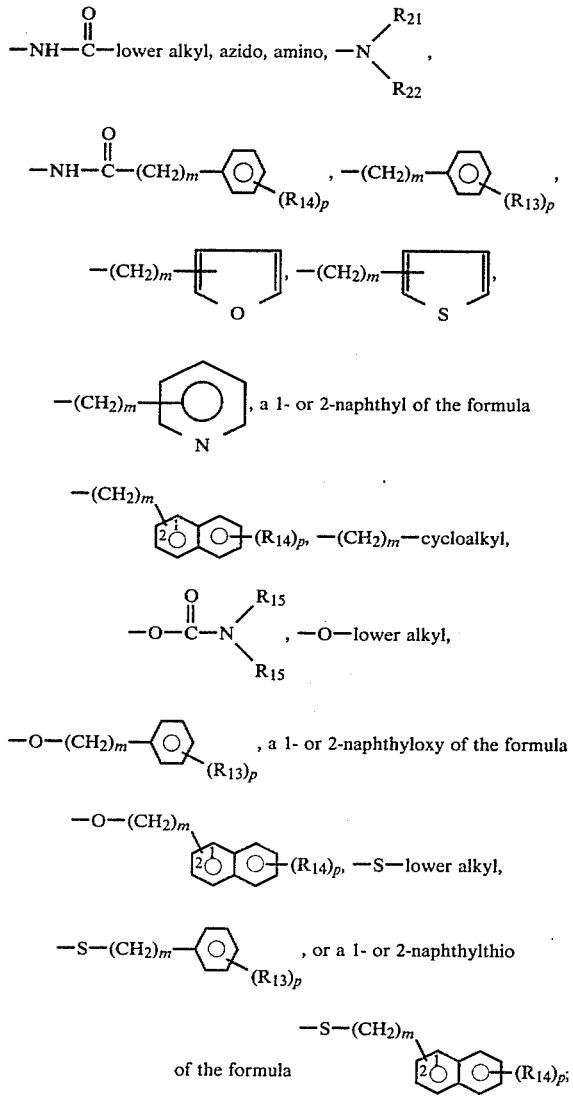

$R_7$ is hydrogen, lower alkyl, halogen, keto, hydroxy, $R_8$ is keto, halogen,

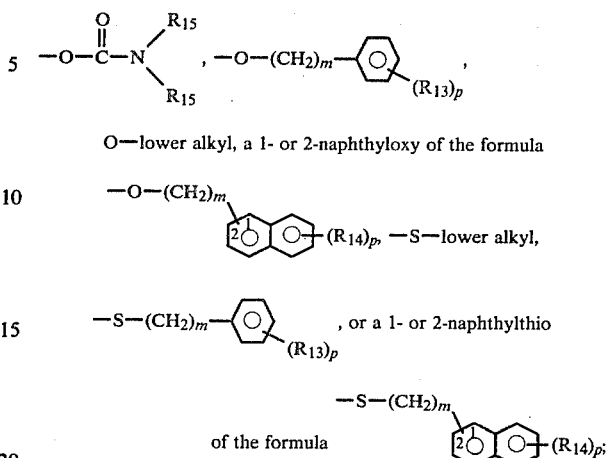

$R_9$ is keto or

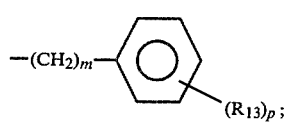

$R_{10}$ is halogen or $-Y-R_{16}$;
$R_{11}$, $R_{11}'$, $R_{12}$ and $R_{12}'$ are independently selected from hydrogen and lower alkyl or $R_{11}'$, $R_{12}$ and $R_{12}'$ are hydrogen and $R_{11}$ is

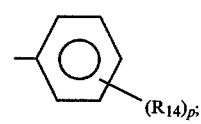

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;
$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;
m is zero, one, two or three;
p is one, two or three provided that p is more than one only if $R_{13}$ or $R_{14}$ is hydrogen, methyl, methoxy, chloro, or fluoro;
$R_{15}$ is hydrogen or lower alkyl of 1 to 4 carbons;
Y is oxygen or sulfur;
$R_{16}$ is lower alkyl of 1 to 4 carbons,

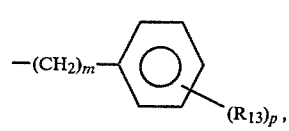

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent;

n is zero or one;
R₅ is hydrogen, lower alkyl, halo substituted lower alkyl, benzyl or phenethyl;
R₃ and R₆ are independently selected from hydrogen, lower alkyl, benzyl, benzhydryl, or

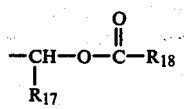

wherein R₁₇ is hydrogen, lower alkyl, or phenyl, and R₁₈ is hydrogen, lower alkyl, lower alkoxy, phenyl, or R₁₇ and R₁₈ taken together are —(CH₂)₂—, —(CH₂)₃—, —CH=CH—, or

R₁ is hydrogen,

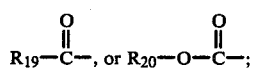

R₁₉ is hydrogen, lower alkyl, halo substituted lower alkyl, amino substituted lower alkyl,

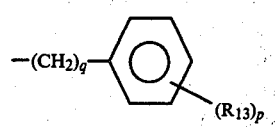

wherein R₁₃ and p are as defined above and q is zero or an integer from 1 to 7, cycloalkyl,

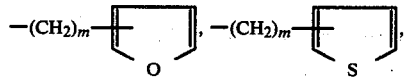

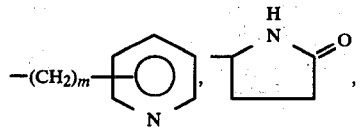

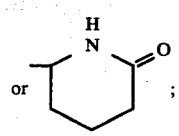

R₂₀ is lower alkyl, phenyl, benzyl or phenethyl;
R₂₁ is lower alkyl, benzyl or phenethyl;
R₂₂ is hydrogen, lower alkyl, benzyl or phenethyl;
R₂ is hydrogen, lower alkyl, lower alkenyl, halo substituted lower alkyl,

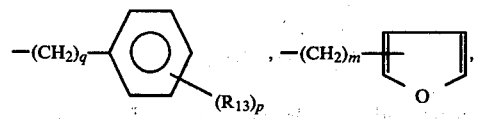

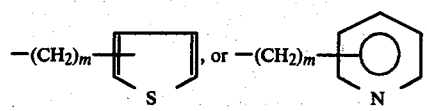

wherein q, R₁₃, p and m are as defined above; and when either or both of R₃ and R₆ are hydrogen a basic addition salt or an amino acid addition salt thereof.

2. A compound of claim 1 wherein R₁ is

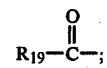

R₁₉ is lower alkyl of 1 to 7 carbons, trifluoromethyl,

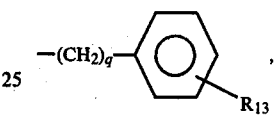

cyclopentyl, cyclohexyl, 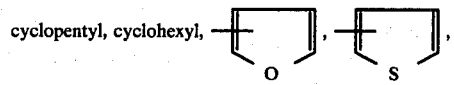

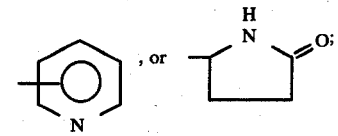

R₃ is hydrogen or

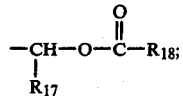

R₅ is hydrogen;
n is zero;
R₂ is lower alkyl of 1 to 7 carbons, or

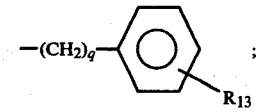

q is zero or an integer from 1 to 4;
R₁₃ is hydrogen, methyl, methoxy, methylthio, chloro, bromo, fluoro, or hydroxy;
R₁₇ is hydrogen or methyl; and
R₁₈ is lower alkyl of 1 to 4 carbons or phenyl.

3. A compound of claim 2 wherein X is

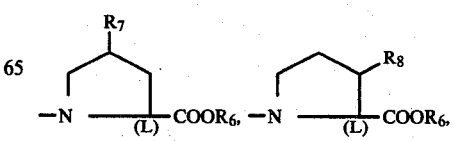

-continued

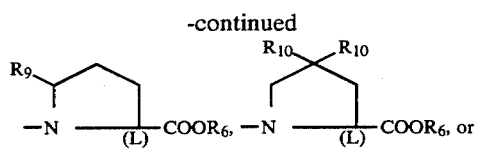
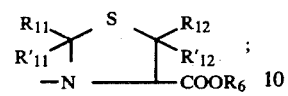

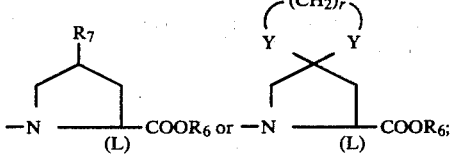

R$_7$ is hydrogen, cyclohexyl,

R$_7$ is hydrogen, hydroxy, amino, lower alkyl of 1 to 4 carbons, cyclohexyl, lower alkoxy of 1 to 4 carbons,

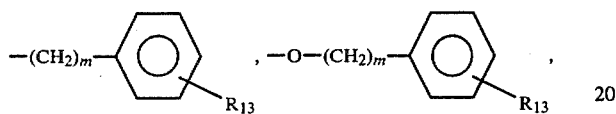
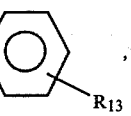

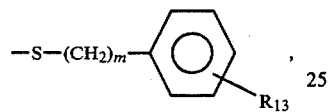

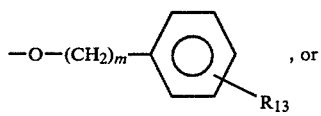

or lower alkylthio of 1 to 4 carbons;
R$_8$ is lower alkoxy of 1 to 4 carbons, lower alkylthio of 1 to 4 carbons,

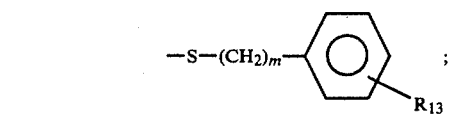

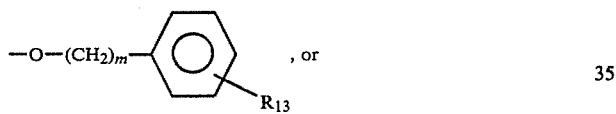

m is zero, one or two;
R$_{13}$ is hydrogen, methyl, methoxy, methylthio, Cl, Br, F, or hydroxy;
Y is O or S;
r is two or three; and
R$_6$ is hydrogen or

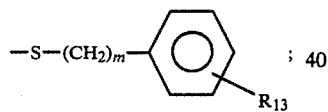

$$-CH_2OCC(CH_3)_3.$$
(with O double bond above C)

5. A compound of claim 4 wherein R$_2$ is

R$_9$ is phenyl, 2-hydroxyphenyl, or 4-hydroxyphenyl;
m is zero, one or two;
R$_{13}$ is hydrogen, methyl, methoxy, methylthio, chloro, bromo, fluoro, or hydroxy;
R$_{10}$ is fluoro, chloro, or —Y—R$_{16}$;
Y is O or S;
R$_{16}$ is lower alkyl of 1 to 4 carbons or the R$_{16}$ groups join to complete an unsubstituted 5- or 6-membered ring or said ring in which one or more of the available carbon atoms has a methyl or dimethyl substituent;
R$_{11}$, R$_{11}'$, R$_{12}$ and R$_{12}'$ are all hydrogen or R$_{11}$ is phenyl, 2-hydroxyphenyl, or 4-hydroxyphenyl, and R$_{11}'$, R$_{12}$ and R$_{12}'$ are all hydrogen;
R$_6$ is hydrogen or

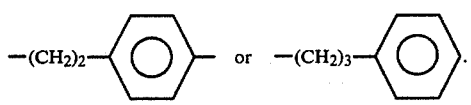

6. A compound of claim 5 wherein R$_{19}$ is

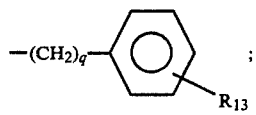

q is zero or an integer from 1 to 4; R$_{13}$ is hydrogen, methyl, methoxy, Cl, Br, F, or hydroxy; and R$_3$ is hydrogen or

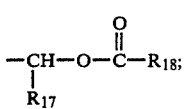

R$_{17}$ is hydrogen or methyl; and
R$_{18}$ is lower alkyl or 1 to 4 carbons or phenyl.
4. A compound of claim 3 wherein X is

7. The compound of claim 6 wherein R$_{19}$ is phenyl; R$_2$ is

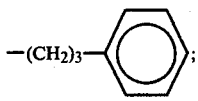

$R_3$ is hydrogen; and X is L-proline.

8. The compound of claim 6 wherein $R_{19}$ is phenyl; $R_2$ is

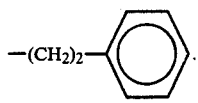

$R_3$ is hydrogen; and X is

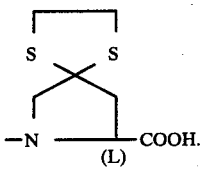

9. The compound of claim 6 wherein $R_{19}$ is phenyl; $R_2$ is

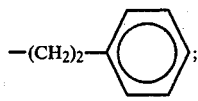

$R_3$ is hydrogen; and X is L-proline.

10. The compound of claim 6 wherein $R_{19}$ is phenyl; $R_2$ is

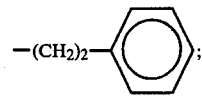

$R_3$ is hydrogen; and X is 4-(phenylmethyl)-L-proline.

11. The compound of claim 6 wherein $R_{19}$ is phenyl; $R_2$ is

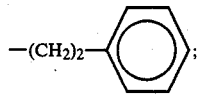

$R_3$ is hydrogen; and X is L-proline, (2,2-dimethyl-1-oxo-propoxy)methyl ester.

12. The lithium salt of the compound of claim 11.

13. A compound of claim 5 wherein $R_{19}$ is lower alkyl of 1 to 7 carbons; and $R_3$ is hydrogen or

14. A compound of claim 13 wherein $R_{19}$ is —(CH$_2$)$_4$—CH$_3$; $R_2$ is

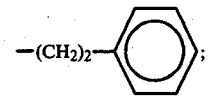

$R_3$ is hydrogen; and X is L-proline.

15. A compound of claim 5 wherein $R_{19}$ is CF$_3$ and $R_3$ is hydrogen or

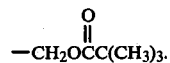

16. The compound of claim 15 wherein $R_2$ is

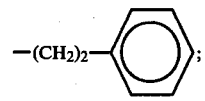

$R_3$ is hydrogen; and X is L-proline.

17. The dilithium salt of the compound of claim 16.

18. A compound of claim 5 wherein $R_{19}$ is cyclopentyl or cyclohexyl; and $R_3$ is hydrogen or

19. A compound of claim 18 wherein $R_{19}$ is cyclopentyl; $R_2$ is

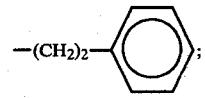

$R_3$ is hydrogen; and X is L-proline.

20. A compound of claim 5 wherein $R_{19}$ is

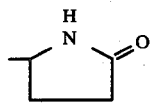

and $R_3$ is hydrogen or

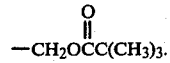

21. The compound of claim 20 wherein $R_2$ is

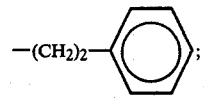

$R_3$ is hydrogen; and X is L-proline.

22. The compound of claim 4 wherein $R_{19}$ is phenyl; $R_2$ is —(CH$_2$)$_5$—CH$_3$; $R_3$ is hydrogen; and X is L-proline.

23. A compound of claim 1 wherein
$R_1$ is hydrogen;
$R_3$ is hydrogen or

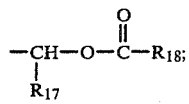

R₅ is hydrogen;
n is zero;
R₂ is lower alkyl of 1 to 7 carbons, or

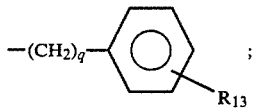

q is zero or an integer from 1 to 4;
R₁₃ is hydrogen, methyl, methoxy, methylthio, chloro, bromo, fluoro, or hydroxy;
R₁₇ is hydrogen or methyl; and
R₁₈ is lower alkyl of 1 to 4 carbons or phenyl.

24. A compound of claim 23 wherein X is

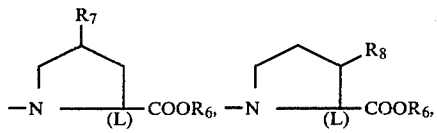

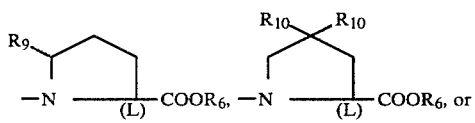

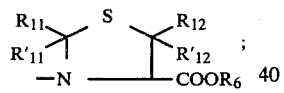

R₇ is hydrogen, hydroxy, amino, lower alkyl of 1 to 4 carbons, cyclohexyl, lower alkoxy of 1 to 4 carbons,

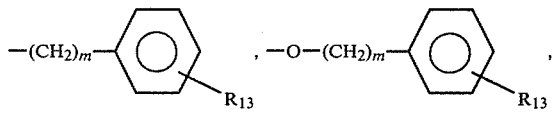

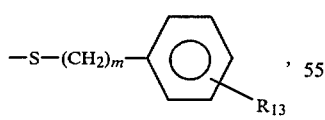

or lower alkylthio of 1 to 4 carbons;
R₈ is lower alkoxy of 1 to 4 carbons, lower alkylthio of 1 to 4 carbons,

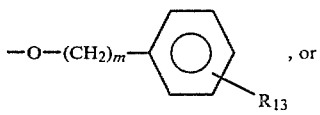

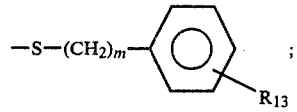

R₉ is phenyl, 2-hydroxyphenyl, or 4-hydroxyphenyl;
m is zero, one or two;
R₁₃ is hydrogen, methyl, methoxy, methylthio, chloro, bromo, fluoro, or hydroxy;
R₁₀ is fluoro, chloro, or —Y—R₁₆;
Y is O or S;
R₁₆ is lower alkyl of 1 to 4 carbons or the R₁₆ groups join to complete an unsubstituted 5- or 6-membered ring or said ring in which one or more of the available carbon atoms has a methyl or dimethyl substituent;
R₁₁, R₁₁', R₁₂ and R₁₂' are all hydrogen or R₁₁ is phenyl, 2-hydroxyphenyl, or 4-hydroxyphenyl, and R₁₁', R₁₂ and R₁₂' are all hydrogen;
R₆ is hydrogen or

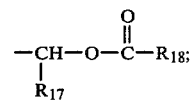

R₁₇ is hydrogen or methyl; and
R₁₈ is lower alkyl of 1 to 4 carbons or phenyl.

25. A compound of claim 24 wherein X is

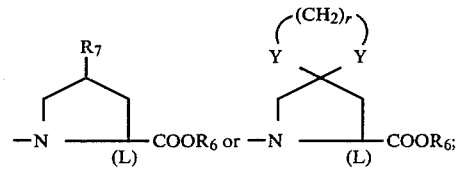

R₇ is hydrogen, cyclohexyl,

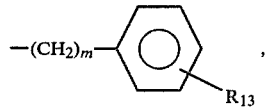

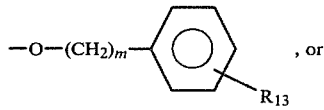

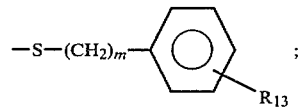

m is zero, one or two;
R₁₃ is hydrogen, methyl, methoxy, methylthio, Cl, Br, F, or hydroxy;
Y is O or S;
r is two or three; and
R₆ is hydrogen or

26. The compound of claim 25 wherein $R_2$ is

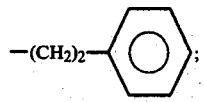

$R_3$ is hydrogen; and X is L-proline.

27. The compound of claim 25 wherein $R_2$ is —(CH$_2$)$_3$—CH$_3$; $R_3$ is hydrogen; and X is L-proline.

28. The compound of claim 25 wherein $R_2$ is —CH$_3$; $R_3$ is hydrogen; and X is L-proline.

29. A compound of claim 1 of the formula

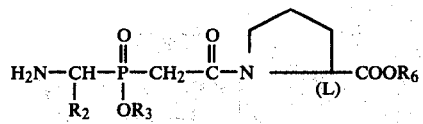

wherein
$R_2$ is lower alkyl of 1 to 7 carbons, or

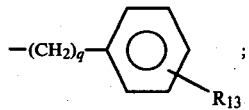

q is zero or an integer from 1 to 4;
$R_{13}$ is hydrogen, methyl, methoxy, methylthio, chloro, bromo, fluoro, or hydroxy; and
$R_3$ and $R_6$ are independently selected from the group consisting of lower alkyl, benzyl, and benzhydryl.

30. The compound of claim 29 wherein $R_2$ is

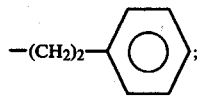

$R_3$ is —C$_2$H$_5$; and $R_6$ is —C(CH$_3$)$_3$.

31. The compound of claim 1 wherein $R_1$ is

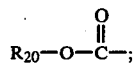

$R_{20}$ is lower alkyl;
$R_3$ is hydrogen or

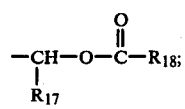

$R_5$ is hydrogen;
n is zero;
$R_2$ is lower alkyl of 1 to 7 carbons, or

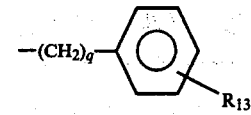

q is zero or an integer from 1 to 4;
$R_{13}$ is hydrogen, methyl, methoxy, methylthio, chloro, bromo, fluoro, or hydroxy;
$R_{17}$ is hydrogen or methyl; and
$R_{18}$ is lower alkyl of 1 to 4 carbons or phenyl.

32. A compound of claim 31 wherein X is

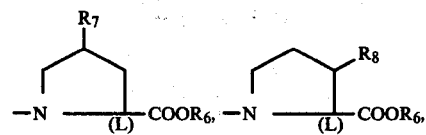

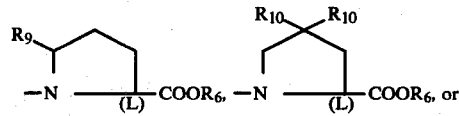

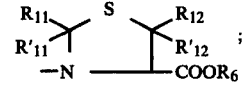

$R_7$ is hydrogen, hydroxy, amino, lower alkyl of 1 to 4 carbons, cyclohexyl, lower alkoxy of 1 to 4 carbons,

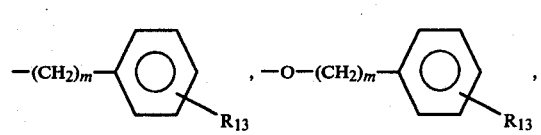

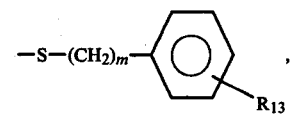

or lower alkylthio of 1 to 4 carbons;
$R_8$ is lower alkoxy of 1 to 4 carbons, lower alkylthio of 1 to 4 carbons,

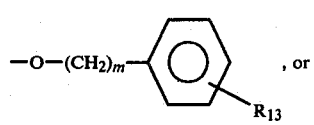

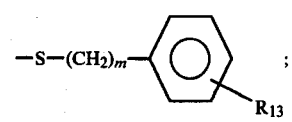

$R_9$ is phenyl, 2-hydroxyphenyl, or 4-hydroxyphenyl;
m is zero, one or two;
$R_{13}$ is hydrogen, methyl, methoxy, methylthio, chloro, bromo, fluoro, or hydroxy;
$R_{10}$ is fluoro, chloro, or —Y—$R_{16}$;
Y is O or S;

$R_{16}$ is lower alkyl of 1 to 4 carbons or the $R_{16}$ groups join to complete an unsubstituted 5- or 6-membered ring or said ring in which one or more of the available carbon atoms has a methyl or dimethyl substituent;

$R_{11}$, $R_{11}'$, $R_{12}$ and $R_{12}'$ are all hydrogen or $R_{11}$ is phenyl, 2-hydroxyphenyl, or 4-hydroxyphenyl, and $R_{11}'$, $R_{12}$ and $R_{12}'$ are all hydrogen;

$R_6$ is hydrogen or

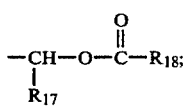

$R_{17}$ is hydrogen or methyl; and
$R_{18}$ is lower alkyl or 1 to 4 carbons or phenyl.

33. A compound of claim 32 wherein X is

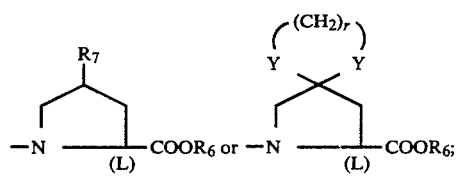

$R_7$ is hydrogen, cyclohexyl,

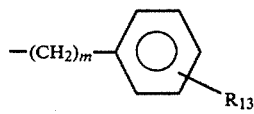

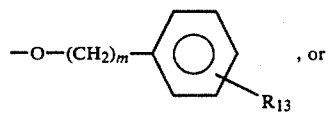, or

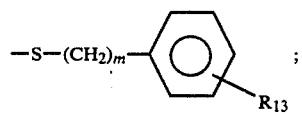;

m is zero, one or two;
$R_{13}$ is hydrogen, methyl, methoxy, methylthio, Cl, Br, F, or hydroxy;
Y is O or S;
r is two or three; and $R_6$ is hydrogen or

34. The compound of claim 33 wherein $R_{20}$ is —$C_2H_5$; $R_2$ is

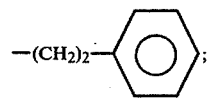;

$R_3$ is hydrogen; and X is L-proline.

35. The compound of claim 1 wherein $R_1$ is

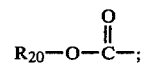

$R_{20}$ is

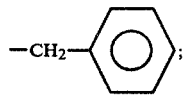;

$R_3$ is lower alkyl or benzyl;
$R_5$ is hydrogen;
n is zero;
$R_2$ is lower alkyl of 1 to 7 carbons or

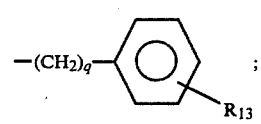;

q is zero or an integer from 1 to 4; and
$R_{13}$ is hydrogen, methyl, methoxy, methylthio, chloro, bromo, fluoro, or hydroxy.

36. A pharmaceutical composition useful for treating hypertension comprising a pharmaceutically acceptable carrier and one or more compounds of claim 1 or pharmaceutically acceptable salts thereof.

37. The method of treating hypertension in a mammalian specie comprising administering an effective amount of the composition of claim 36.

* * * * *